US012661259B2

(12) United States Patent
Kerber et al.

(10) Patent No.: US 12,661,259 B2
(45) Date of Patent: Jun. 23, 2026

(54) THERAPEUTIC METHODS FOR TREATING TISSUE

(71) Applicant: INMODE LTD, Yokneam (IL)

(72) Inventors: Martin Kerber, Englewood, CO (US);
Stacie Bell, Englewood, CO (US);
James Atkinson, Greenwood Village,
CO (US)

(73) Assignee: INMODE LTD, Yokneam (IL)

( * ) Notice: Subject to any disclaimer, the term of this
patent is extended or adjusted under 35
U.S.C. 154(b) by 1104 days.

(21) Appl. No.: 17/587,993

(22) Filed: Jan. 28, 2022

(65) Prior Publication Data

US 2022/0151826 A1     May 19, 2022

Related U.S. Application Data

(63) Continuation-in-part of application No. 16/482,581,
filed as application No. PCT/US2018/016266 on Jan.
31, 2018, now abandoned, application No.
17/587,993 is a continuation-in-part of application
No. 16/454,578, filed on Jun. 27, 2019, now Pat. No.
1,151,110.

(60) Provisional application No. 63/143,698, filed on Jan.
29, 2021, provisional application No. 62/452,889,
filed on Jan. 31, 2017, provisional application No.
62/690,534, filed on Jun. 27, 2018.

(51) Int. Cl.
*A61F 7/12*     (2006.01)
*A61F 7/00*     (2006.01)
*A61F 7/02*     (2006.01)

(52) U.S. Cl.
CPC .......... *A61F 7/12* (2013.01); *A61F 2007/005*
(2013.01); *A61F 2007/0063* (2013.01); *A61F*
*2007/0296* (2013.01)

(58) Field of Classification Search
CPC .................. A61F 7/12; A61F 2007/005; A61F
2007/0063; A61F 2007/0296; A61F 7/007
See application file for complete search history.

(56) References Cited

U.S. PATENT DOCUMENTS

| | | | | |
|---|---|---|---|---|
| 2007/0233191 A1* | 10/2007 | Parmer | .............. | A61B 18/1485 607/1 |
| 2010/0049186 A1* | 2/2010 | Ingle | .................. | A61B 18/1485 606/33 |
| 2011/0178584 A1* | 7/2011 | Parmer | .................. | A61B 90/06 607/101 |
| 2015/0165241 A1* | 6/2015 | Burdette | .................. | A61B 8/12 601/3 |
| 2015/0366747 A1* | 12/2015 | Lei | .......................... | A61H 19/44 600/38 |
| 2017/0071651 A1* | 3/2017 | Allan | ...................... | A61B 18/02 |
| 2018/0000533 A1* | 1/2018 | Boll | ................... | A61B 18/1206 |

* cited by examiner

*Primary Examiner* — Joseph A Stoklosa
*Assistant Examiner* — Adam J Avigan
(74) *Attorney, Agent, or Firm* — K&L Gates LLP

(57) ABSTRACT

A method for treating urinary stress incontinence. The method includes non-invasively cooling target tissue during a first cooling step, a non-cooling step, and non-invasively cooling the target tissue in a second cooling step. The first cooling step, the non-cooling step, and the second cooling step are performed at predetermined temperatures for a predetermined period of time.

23 Claims, 11 Drawing Sheets

Position 2
1-3 cm
10 pulses

Position 4
2-4 cm
10 pulses

Position 1
0-2 cm
100
pulses

Position 3
1-3 cm
100
pulses

SUBJECT DISPOSITION:

| | GROUP 1 (N) | GROUP 2 (N) | TOTAL (N) |
|---|---|---|---|
| RANDOMIZED & TREATED SUBJECTS | 21 | 14 | 35 |
| 12-MONTH FOLLOW-UP (TO DATE): RANDOMIZED & TREATED | 7 | 13 | 20 |

METHODS:

- 1-HOUR PAD WEIGHT TEST[3]
- 0-15 MIN: DRINKING 500 ML OF SODIUM-FREE LIQUID, RESTING
- 15-45 MIN: WALKING WITH STAIR CLIMBING UP/DOWN 1 FLIGHT
- 45-60 MIN: STANDING UP FROM SITTING (10X), COUGHING VIGOROUSLY (10X), RUNNING ON THE SPOT (1 MIN), BENDING TO PICK UP SMALL OBJECT FROM THE FLOOR (5X), WASHING HANDS IN RUNNING WATER (1 MIN)

CMRF TREATMENT FOR SUI RESULTS IN A REDUCTION IN LEAKAGE VOLUME ON 1-HOUR PAD WEIGHT TEST

| GROUP | BASE-LINE PAD WEIGHT | PAD WEIGHT LEAKAGE VOLUME % OF SUBJ W/ >50% REDUCTION IN PAD WEIGHT FROM BASELINE | | | | |
|---|---|---|---|---|---|---|
| | | MONTH 1 | MONTH 4 | MONTH 6 | MONTH 12 | |
| ALL SUBJECTS | 7.29 G (N=35) | 2.15 G 56% (N=34) | 1.27 G 73% (N=33) | 1.69 G 69% (N=29) | 3.20 G 60% (N=20) | |
| GROUP A: 1 SUI TX | 7.24 G (N=21) | 2.25 G 60% (N=20) | 1.11 G 68% (N=19) | 1.81 G 69% (N=16) | 2.57 G 71% (N=7) | |
| GROUP B: 2 SUI TX | 7.36 G (N=14) | 2.00 G 50% (N=14) | 1.50 G 79% (N=14) | 1.54 G 69% (N=13) | 3.54 G 54% (N=13) | |

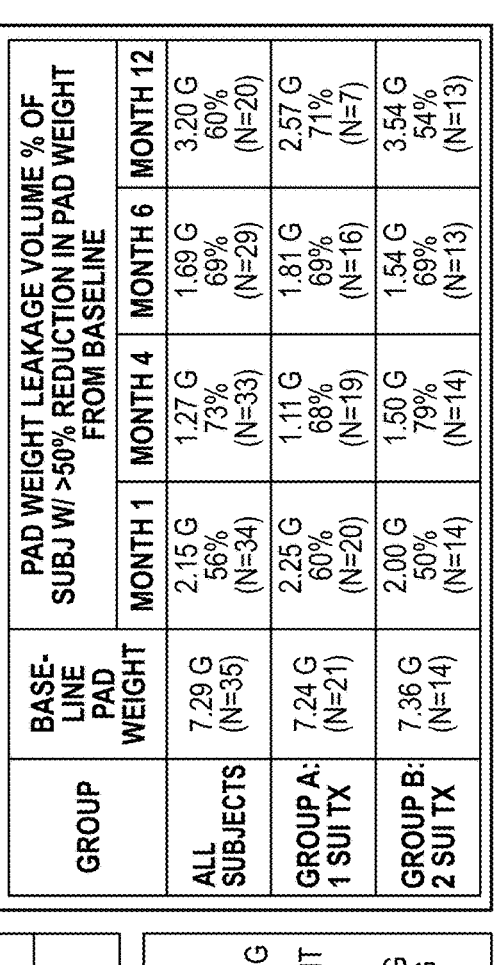

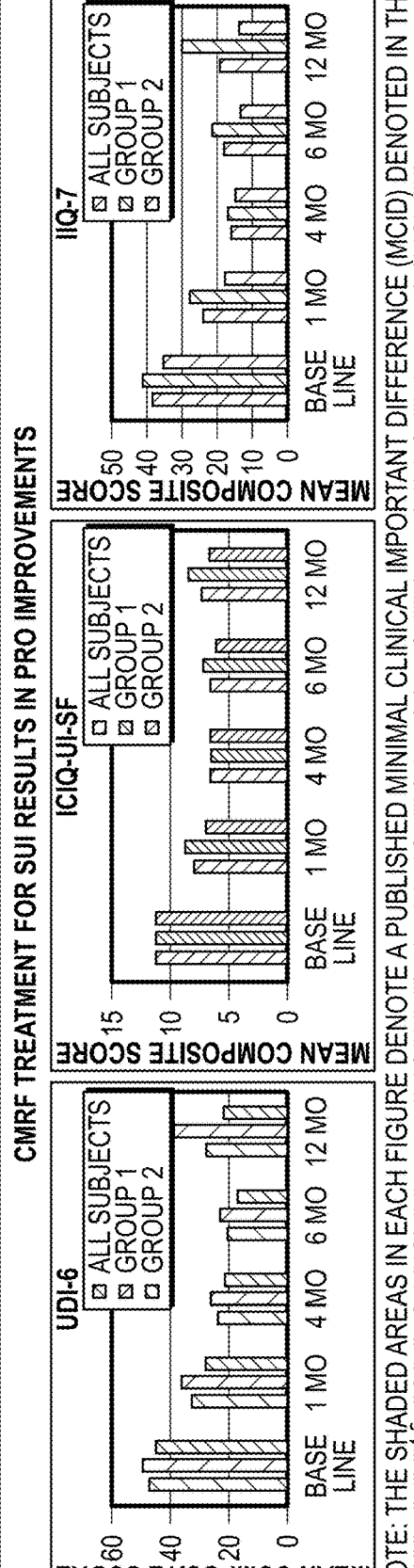

CMRF TREATMENT FOR SUI RESULTS IN PRO IMPROVEMENTS

NOTE: THE SHADED AREAS IN EACH FIGURE DENOTE A PUBLISHED MINIMAL CLINICAL IMPORTANT DIFFERENCE (MCID) DENOTED IN THE LITERATURE[4,5]. FOR EACH FIGURE: N=35 (BASELINE), N=34 (1MONTH), N=33 (4 MONTH), N=29 (6 MONTH), N=20 (12MONTH)

FIG. 5

DESIGN: PROSPECTIVE, RANDOMIZED, DOUBLE-BLIND TRIAL, N=99
- ACTIVE: CMRF (RF AND COOLING) / SHAM: CRYO (COOLING ONLY)
- PRE-MENOPAUSAL WOMEN WITH MILD-TO-MODERATE SUI (5G ML - 50G ML LEAKAGE)

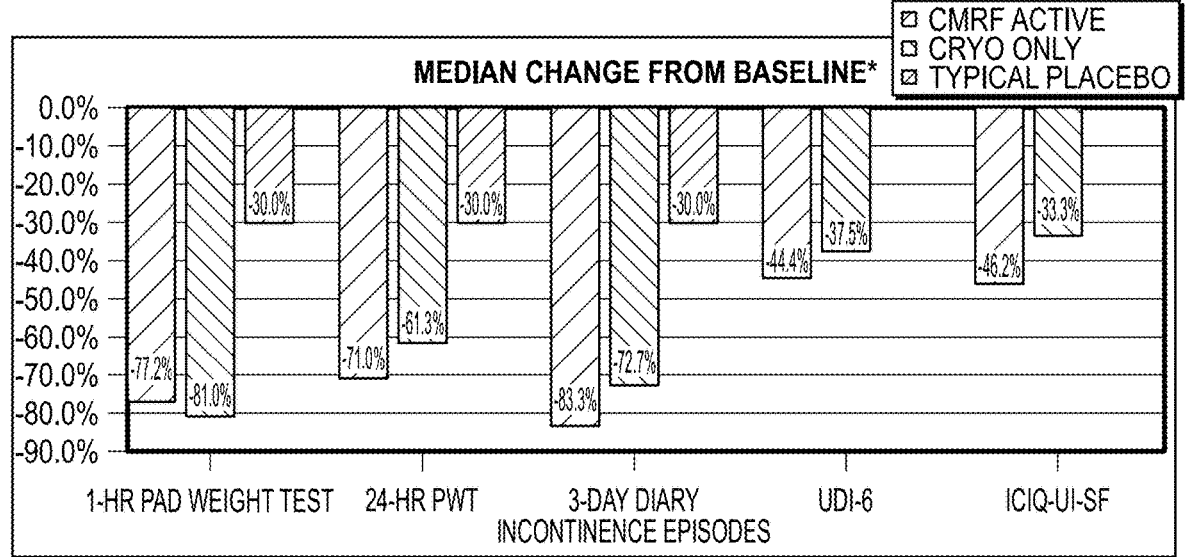

•PERCENTAGE CHANGE RESULTS BASED UPON OBSERVED CASE DATA.
UDI-6: RANGE OF 0 (NO PROBLEM AT ALL) TO 100 (MAXIMUM PROBLEM)
IQOL: RANGE OF 0 (MAXIMUM PROBLEM) TO 100 (NO PROBLEM AT ALL)
IQAL-UI-SF: RANGE OF 0 (NO PROBLEM AT ALL) TO 21 (MAXIMUM PROBLEM)

FIG. 6

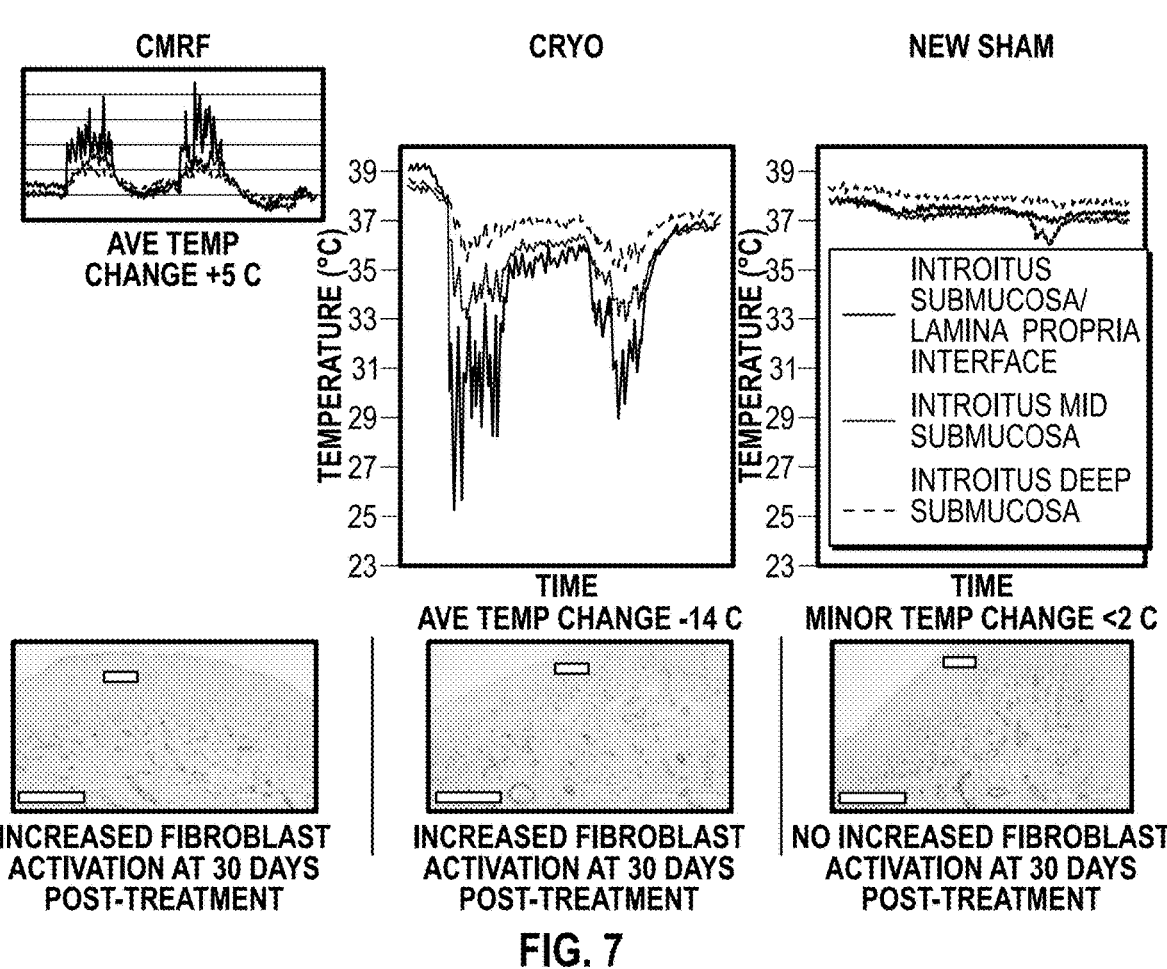

CMRF       CRYO       NEW SHAM

AVE TEMP CHANGE +5 C

AVE TEMP CHANGE -14 C     MINOR TEMP CHANGE <2 C

INTROITUS SUBMUCOSA/ LAMINA PROPRIA INTERFACE

INTROITUS MID SUBMUCOSA

INTROITUS DEEP SUBMUCOSA

INCREASED FIBROBLAST ACTIVATION AT 30 DAYS POST-TREATMENT

INCREASED FIBROBLAST ACTIVATION AT 30 DAYS POST-TREATMENT

NO INCREASED FIBROBLAST ACTIVATION AT 30 DAYS POST-TREATMENT

FIG. 7

DESIGN: PROSPECTIVE, RANDOMIZED, BLINDED TRIAL

- 3 SITES, 36 PATIENTS, 1:1:1 RATIO
- CMRF (RF AND COOLING) VS CRYO (COOLING ONLY) VS NEW SHAM TIP (INERT)
- PRE-MENOPAUSAL WOMEN WITH MILD-TO-MODERATE SUI (5G ML - 50G ML LEAKAGE)

RESULTS: PRIMARY ENDPOINT ACHIEVED

- CFB IN 1HR PAD WEIGHT TEST AT 5-MONTHS POST TREATMENT
- SECONDARY ENDPOINTS SHOWED NO DIFFERENTIATION BETWEEN GROUPS AND NO DEVICE-RELATED SAFETY ISSUES REPORTED

|  | BASELINE | 5 MONTH | CFB |
|---|---|---|---|
| MEAN CMRF ACTIVE | 14.25 | 7.71 | -6.55 |
| MEDIAN CMRF ACTIVE | 11.60 | 6.50 | -9.50 |
| MEAN CRYO SHAM | 12.38 | 3.10 | -9.28 |
| MEDIAN CRYO SHAM | 9.60 | 3.15 | -6.80 |
| MEAN INERT SHAM | 7.52 | 6.45 | -1.07 |
| MEDIAN INERT SHAM | 6.40 | 3.10 | -4.40 |

FIG. 8

THERAPEUTIC METHODS FOR TREATING TISSUE

CROSS REFERENCE TO RELATED APPLICATIONS

This application claims priority to U.S. Provisional Patent Application No. 63/143,698, filed Jan. 29, 2021. This application is a continuation-in-part of U.S. patent application Ser. No. 16/482,581, filed Jul. 31, 2019, which claims priority to International Patent Application No. PCT/US2018/016266, filed Jan. 31, 2018, which claims the benefit of priority of U.S. Provisional Patent Application No. 62/452,889, filed Jan. 31, 2017. This application is a continuation-in-part of U.S. patent application Ser. No. 16/454, 578, filed Jun. 27, 2019, which claims the benefit of priority of U.S. Provisional Patent Application No. 62/690,534, filed Jun. 27, 2018. The entire contents of each of the aforementioned applications is hereby incorporated herein by reference in its entirety.

TECHNICAL FIELD

The field of the currently claimed embodiments of this invention relates to a method and apparatus for treating urinary stress incontinence, such as by cooling a target tissue to a therapeutic temperature.

BACKGROUND

Urinary incontinence is a socially disabling condition that affects millions of women of all ages and ethnicities. Urinary stress incontinence is defined by the involuntary loss of urine during increased intra-abdominal pressure in the absence of a detrusor contraction. Increased intra-abdominal pressure can be caused by coughing, sneezing, laughing, exercising, and lifting heavy objects, for example. Urinary stress incontinence is the most common type of female urinary incontinence, affecting more than an estimated 7 million women in the United States. Current methods of treatment of urinary stress incontinence are al invasive to some degree. Accordingly, there is a need for a non-invasive, non-pharmaceutical treatment for urinary stress incontinence in women.

BRIEF SUMMARY

According to an aspect of the present disclosure, a method for treating urinary stress incontinence with therapeutic cooling a plurality of target tissues in a subject may include non-invasively cooling the plurality of target tissue and remodeling one or more submucosal regions of the plurality of target tissues to treat the subject for urinary stress incontinence. The plurality of target tissues are located within 4 predetermined quadrants around a vaginal canal. The plurality of target tissues include 40 target tissue locations, such that each of the 4 predetermined quadrants includes 10 target tissue locations. The non-invasively cooling includes applying at least 10 treatment passes in each of the 4 predetermined quadrants. Each of the at least 10 treatment passes includes applying, in a predetermined order, 1 to 5 cooling periods to each of the 10 target tissue locations in each of the 4 predetermined quadrants. The non-invasively cooling a plurality of target tissues further includes applying up to 20 treatment passes to two or more target tissue locations located alongside a urethra of the subject, each of said 20 treatment passes including applying a cooling period.

According to an aspect of the present disclosure, the applying at least 10 treatment passes in each of the 4 predetermined quadrants includes executing a first series of 5 treatment passes in each of the 4 predetermined quadrants and executing a second series of 5 treatment passes in each of the 4 predetermined quadrants. The first series of 5 treatment passes in each quadrant is completed before the second series of 5 treatment passes in each of the 4 predetermined quadrants is initiated. Each of the first series of 5 treatment passes and each the second series of 5 treatment passes includes applying in a predetermined order one cooling period to each of the 10 target tissue locations in each of the 4 predetermined quadrants.

According to an aspect of the present disclosure, the applying up to 20 treatment passes to two or more target tissues located alongside the urethra of the subject includes delivering a first series of 10 treatment passes to the two or more target tissues located alongside the urethra and delivering a second series of 10 treatment passes to the two or more target tissues located alongside the urethra. The first series of 10 or more treatment passes is delivered after executing the first series of 5 treatment passes in each of the 4 predetermined quadrants. he second series of 10 or more treatment passes is delivered after executing the second series of 5 treatment passes in each of the 4 predetermined quadrants.

According to an aspect of the present disclosure, executing each treatment pass of the first series of 5 treatment passes in each of the 4 predetermined quadrants includes applying, in a predetermined order, a cooling step to each of a first set of 5 target tissue locations in each of the 4 predetermined quadrants such that each target tissue location of the first set of 5 target tissue locations at least partially overlaps with an adjacent target tissue location. Executing each treatment pass of the second series of 5 treatment passes in each of the 4 predetermined quadrants includes applying in a predetermined order a cooling step to each of a second set of 5 target tissue locations in each of the 4 predetermined quadrants, such that each target tissue location of the second set of 5 target tissue locations at least partially overlaps with an adjacent target tissue location.

According to an aspect of the present disclosure, each target tissue location of the second set of 5 target tissue locations in each of the 4 predetermined quadrants is proximal to each target tissue location of the first set of 5 target tissue locations in each of the 4 predetermined quadrants.

According to an aspect of the present disclosure, the first series of 10 treatment passes and the second series of 10 treatment passes are delivered to two target tissue regions, a first target tissue region of the two target tissue regions is located on a first side of the urethra, and a second target tissue region of the two target tissue regions is located on a second side of the urethra. Each treatment pass of the first series of 10 treatment passes and the second series of 10 treatment passes are applied in an alternating manner to the first target tissue region and to the second target tissue region.

According to an aspect of the present disclosure, executing the first series of 5 treatment passes in each of the 4 predetermined quadrants includes executing 5 treatment passes in a first quadrant, executing 5 treatment passes in a second quadrant after executing 5 treatment passes in the first quadrant, executing 5 treatment passes in a third quadrant after executing 5 treatment passes in the second quadrant, and executing 5 treatment passes in a fourth quadrant after executing 5 treatment passes in the third quadrant.

According to an aspect of the present disclosure, the 4 predetermined quadrants include a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and wherein the urethra of the subject is located at the 12 o'clock position.

According to an aspect of the present disclosure, each of the cooling periods is applied for up to 2.0 seconds.

According to an aspect of the present disclosure, each of the cooling periods is applied for up to 1.5 seconds.

According to an aspect of the present disclosure, each of the cooling periods cools the each of the plurality of target tissues to a surface temperature of between 13 degrees Celsius and 35 degree Celsius.

According to an aspect of the present disclosure, each of the 10 treatment passes and each of the 20 treatment passes includes a non-cooling step following each of the cooling periods.

According to an aspect of the present disclosure, the non-cooling step includes non-invasively heating each of the plurality of target tissues for a period of time.

According to an aspect of the present disclosure, the non-invasively heating each of the plurality of target tissues for a period of time includes delivering radiofrequency energy to each of the plurality of target tissues.

According to an aspect of the present disclosure, the non-invasively heating each of the plurality of target tissues for a period of time includes heating each of the plurality of target tissues to a surface temperature between 18.0 degrees Celsius to 43.0 degrees Celsius for between 0.0-8.0 seconds.

According to an aspect of the present disclosure, the non-cooling step is followed by a second cooling step.

According to an aspect of the present disclosure, the second cooling step is applied for between 2.0 seconds and 8.0 seconds.

According to an aspect of the present disclosure, the second cooling step cools each of the plurality of target tissues to a surface temperature of between 13 degrees Celsius and 35 degrees Celsius.

According to an aspect of the present disclosure, the plurality of target tissues are located at a first position, a second position, a third position, and a fourth position, and wherein the first position is located 0 to 2 cm beyond the hymenal ring, the second position is located 1 to 3 cm beyond the hymenal ring, the third position is located 1 to 3 cm beyond the hymenal ring, and the fourth position is located 2 to 4 cm beyond the hymenal ring.

According to an aspect of the present disclosure, the at least 10 treatment passes includes one hundred passes at the first position, ten passes at the second position, one hundred passes at the third position, and ten passes at the fourth position.

According to an aspect of the present disclosure, the remodeling of the one or more submucosal regions of the plurality of target tissues to treat the subject for urinary stress incontinence is caused only by the non-invasive cooling.

According to an aspect of the present disclosure, non-invasively cooling is the only energy application to the plurality of target tissues.

According to an aspect of the present disclosure, non-invasively cooling is the dominate energy application to the plurality of target tissues, such that, the non-invasive cooling provides the treatment of the urinary stress incontinence and any other energy application applied that is not non-invasive cooling does not provide the treatment of the urinary stress incontinence.

BRIEF DESCRIPTION OF THE DRAWINGS

Features and advantages of the present disclosure will be apparent from the following description of various exemplary embodiments, as illustrated in the accompanying drawings, wherein like reference numbers generally indicate identical, functionally similar, and/or structurally similar elements.

FIG. 5 illustrates tables and graphs of data from preliminary studies comparing a cold-treatment protocol to a heat-treatment protocol, according to an embodiment of the present disclosure.

FIG. 6 illustrates a graphical representation of the data from FIG. 5, according to an embodiment of the present disclosure.

FIG. 7 illustrates various graphs showing results from in-vivo tissue temperature changes and 30-day post-treatment histopathology of a cold-treatment protocol, according to an embodiment of the present disclosure.

FIG. 8 is a table showing results from a three-arm study using a cold-treatment protocol, according to an embodiment of the present disclosure.

DETAILED DESCRIPTION

Figure 1A:
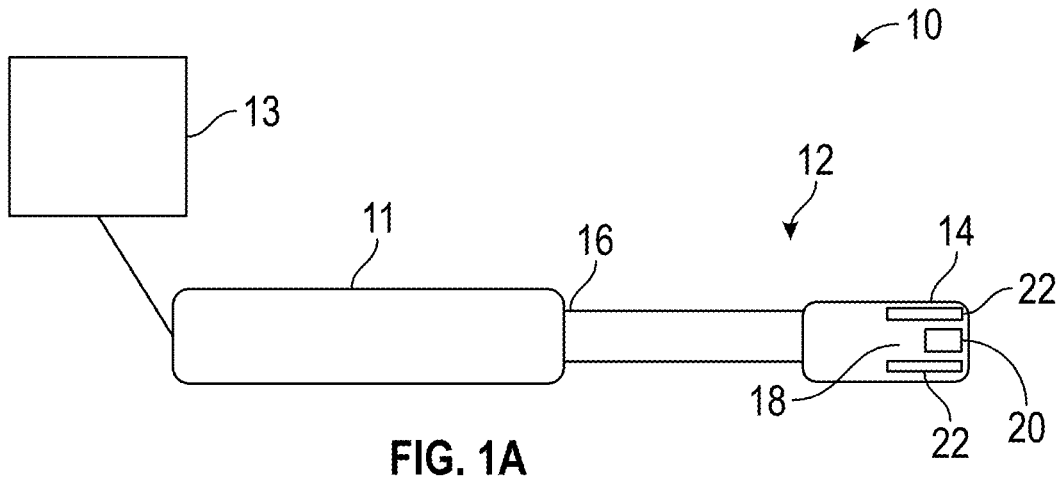
FIG. 1A illustrates an apparatus for applying a cooling agent and/or a heating agent to a target tissue, according to an embodiment of the present disclosure.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Non-invasive, targeted and therapeutic approaches are provided for activating remodeling in a wound and/or tissue to better promote wound healing and/or reduce the formation of scar tissue. The devices, systems and methods provide a minimally invasive way to treat, for example, aesthetic injuries or flaws of a target tissue.

Heat shock proteins (HSPs) and cold shock proteins (CSPs) are families of proteins that are produced by cells in response to exposure to stressful conditions. HSPs were first described in relation to heat shock, but are now known to also be expressed during other stresses including exposure to cold, UV light, and during wound healing or tissue remodeling. Indeed, HSPs and the various biological processes they are associated with are recognized to be active players in tissue remodeling.

CSPs are proteins having a cold-shock domain (CSD) of about 70 amino acids which has been found in prokaryotic and eukaryotic DNA-binding proteins. Part of this domain is highly similar to the RNP-1 RNA-binding motif. CSPs are expressed in a cell or tissue when temperatures fall below that cell or tissue's normal temperature. For instance, when *Escherichia coli* is exposed to a temperature drop from 37 to 10 degrees Celsius, a 4-5 hour lag phase occurs, after which growth is resumed at a reduced rate. During the lag phase, the expression of around 13 proteins, which contain cold shock domains is increased 2-10 fold. These so-called "cold shock" proteins are thought to help the cell to survive in temperatures lower than optimum growth temperature, by contrast with heat shock proteins, which help the cell to survive in temperatures greater than the optimum, possibly by condensation of the chromosome and organization of the prokaryotic nucleoid. Although the role of CSPs in tissue remodeling is unclear, it is clear that these proteins have an effect on the biological processes of cooled cells and tissues and a role for CSPs in tissue remodeling might exist.

HSPs in a wounded tissue can be stimulated by exposing the tissue to cold or heat. Unfortunately, care has to be taken to avoid ablation of the tissues as a result of extremely cold or hot temperatures as occurs during cryoablation or catheter ablation, respectively. This is not desirable when seeking to promote wound healing and limiting the formation of scar tissue and improving the aesthetic appearance of a wound once it heals.

Cryoablation and catheter ablation result in the destruction of tissue. Traditional methods and devices for cryo or thermal ablation result in the destruction of tissues. For example, during cryoablation, hollow needles (cryoprobes) are used to contact and cool target tissues to temperatures below freezing. These cryoprobes are cooled by circulating cooled, thermally conductive fluids within them. Cryoablation ultimately leads to apoptosis of cells within a target tissue, resulting in the destruction of regions within the target tissue. During thermal ablation, a catheter is used to contact and deliver a heating source to a target tissue, resulting in heating of the tissue to a temperature sufficiently high enough to cause destruction of the tissue. In short, traditional methods and devices for cryo and thermal ablation are invasive and result in the destruction of target tissues. By contrast, devices described herein (and methods of using such devices) are designed to be minimally invasive and to avoid or minimize tissue destruction.

Apparatus and System

An example probe suitable for use in practicing the methods of the invention includes a non-invasive probe for promoting correction of an aesthetic or functional defect in a target tissue, having a treatment tip configured for non-invasive contact with a surface of a target tissue. The treatment tip includes: an epithelium-contacting treatment surface; a cooling element in thermal communication with the epithelium-contacting treatment surface; and a heating element in thermal communication with the epithelium-contacting treatment surface. The non-invasive probe also has a controller in communication with the cooling element and the heating element. The controller is configured to control the cooling element to cool the epithelium-contacting treatment surface to a predetermined temperature. The controller is also configured to control the cooling element and the heating element to maintain the predetermined temperature for a predetermined period of time to induce wound healing in the target tissue.

Other suitable probes include the non-invasive probe above, where the epithelium-contacting treatment surface has a length of between 1 mm and 30 mm and a width of between 0.5 cm and 2.0 cm.

Other suitable probes include the non-invasive probe above, where the controller is configured to activate the cooling element for a first period of time and to activate the heating element for a second period of time, such that the first period of time overlaps at least partially with the second period of time.

Other suitable probes include the non-invasive probe above, where the controller is configured to activate the cooling element for a first period of time and to activate the heating element for a second period of time, such that the first period of time commences and ends prior to commencement of the second period of time.

Other suitable probes include the non-invasive probe above, where the controller is configured to activate the cooling element for a first period of time, to activate the heating element for a second period of time, and to activate the cooling element for a third period of time such that such that the first period of time overlaps at least partially with the second period of time, and the second period of time overlaps at least partially with the third period of time.

Other suitable probes include the non-invasive probe above, where the controller is configured to activate the cooling element for a first period of time, to activate the heating element for a second period of time, and to activate the cooling element for a third period of time such that such that the first period of time commences and ends prior to commencement of the second period of time, and the second period of time commences and ends prior to commencement of the third period of time.

Other suitable probes include the non-invasive probe above, where the heating element is a monopolar or bipolar radiofrequency (RF) energy heating element.

Other suitable probes include the non-invasive probe above, where the cooling element is configured to apply cooling to a surface of the target tissue. Applying cooling to the tissue can take various forms. For example, in one aspect the cooling is provided to the tissue by way of an applicator, such as a tip, and the cryogen is applied to the applicator or tip and the applicator or tip contacts the tissue. The cryogen can be applied inside the applicator to chill the tip or the back of an electrode(s). Preferably with mucosal tissue, the cryogen is not applied directly to the tissue but rather through the applicator.

Other suitable probes include the non-invasive probe above, where the cooling agent is selected from the following: compressed liquid $CO_2$, compressed liquid $NO_2$, a hydrofluorocarbon, water, a thermoelectric cooler and an ultra-low temperature cryogen.

Cooling and applying cooling in accordance with the principles of the invention can include cooling using a treatment tip that applies cooling through contact, such as applying a cooled treatment tip, applying a cooling agent and/or composition, including directly and indirectly to the tissue or surface, and all of these modalities for applying cooling can be referred to as applying cooling, a cooling agent or otherwise, interchangeably for purposes of this disclosure, although each modality may have advantages relative to the others. As indicated above, with mucosal tissue it is preferred to apply cooling to the tissue by way of an intermediary, such as a chilled tip, and not applying the cryogen material directly to the tissue. Cooling can be applied to the tissue sequentially with heating and/or simultaneously with heating.

Figure 1B:
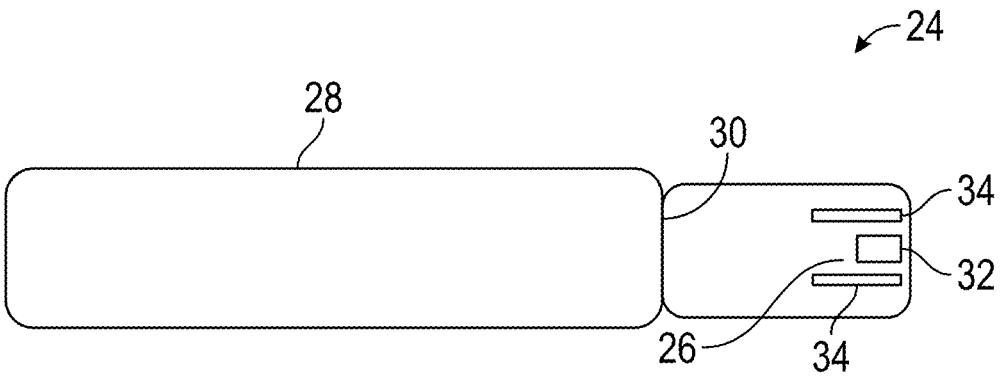
FIG. 1B illustrates an apparatus for applying a cooling agent and/or a heating agent to the target tissue, wherein the treatment surface extends to the proximal portion of the apparatus, according to an embodiment of the present disclosure.

Exemplary probes are shown in FIGS. 1A and 1B, and modifications can be made in order to treat the target tissue effectively and efficiently. FIG. 1A shows an exemplary treatment device 10 for promoting correction of an aesthetic or functional defect in a target tissue. A probe is shown generally at reference numeral 12 to promote correction of an aesthetic or functional defect in a target tissue. The probe 12 has a treatment tip 14 configured for non-invasive contact with a surface of a target tissue, and has a proximal end 11 coupled by an arm 16 to the distal end 14. The treatment tip includes an epithelium-contacting treatment surface 18, a cooling element 20 in thermal communication with the epithelium-contacting treatment surface 18 and a radio frequency (RF) energy heating element 22 in thermal communication with the epithelium-contacting treatment surface 18. The RF energy heating element 22 may be a monopolar or bipolar RF energy heating element. One of skill in the art can envision that the cooling element 20 and the heating element 22 are arranged in varying configurations and can also be positioned at various distances from one another. In some cases, the cooling and heating elements are proximate to one another. In other cases, they can be overlapping. Yet in other cases they can be separated by a desired distance. In accordance with the principles of the inventions herein, a controller 13 in communication with the probe controls the parameters for the treatment of at least one aesthetic or functional defect. At least one aesthetic or functional defect treatment parameter is selected to achieve a predetermined temperature for a predetermined time period in a target tissue to induce remodeling of the target tissue and promote wound healing. The controller coupled to the probe is configured to cool the target tissue based on the at least one aesthetic or functional defect treatment parameter to induce a remodeling of the target tissue for improvement of the aesthetic or functional defect. The distal end 14 of probe 12 has a treatment surface 18 for contacting the target tissue. In some embodiments, the controller 13 can be disposed within the proximal end 11 of the probe 12. In some embodiments, the proximal end 11 of the probe 12 may form a handle to allow a user to hold and manipulate the probe 12 during treatment.

As shown in FIG. 1A, the treatment surface 18 according to some embodiments includes a single treatment surface. The treatment surface 18 may be flat, or may be curved or angled to achieve better contact with the surface of the target tissue. In some embodiments, the treatment surface, which comes into contact with surface regions of the target tissues, may have a total surface area between about 0.5 cm$^2$ and 6 cm$^2$. The total length of the treatment surface area can be between about 1 mm and 30 mm (or between 0.1 cm and 3 cm), and the total width can be between about 0.5 cm and 2.0 cm. One of skill in the art may contemplate other lengths and widths that are appropriate for treating specific target tissues, and would understand the embodiments of the invention to include devices having these configurations.

A probe 24 according to some embodiments is shown in FIG. 1B. The probe 24 includes an epithelium-contacting treatment surface 26 that extends all the way to the proximal portion 28 of the probe 24. The treatment surface 26 may be directly coupled to the proximal portion 28 at the proximal end 30 of the treatment surface 26, or may be joined to the proximal portion 28 by a connecting arm, as shown in FIG. 1A. The treatment tip includes a cooling element 32 in thermal communication with the epithelium-contacting treatment surface and a heating element 34 in thermal communication with the epithelium-contacting treatment surface. One of skill in the art can envision that the cooling element and the heating element are arranged in varying configurations and can also be positioned at various distances from one another. In some cases, the cooling and heating elements are proximate to one another. In other cases, they can be overlapping. Yet in other cases they can be separated by a desired distance. There can also be a plurality of cooling and/or heating elements positioned on the treatment surface. The treatment surface 26 may have a total surface area between about 0.5 cm$^2$ and 6 cm$^2$. The total length of the treatment surface can be between about 0.1 cm and about 6 cm. The total width of the treatment surface according to some embodiments can be between about 0.5 cm and about 3.0 cm. One of skill in the art may contemplate other lengths and widths that are appropriate for treating target tissue, and would understand the embodiments of the invention to include devices having these dimensions.

The probe may further include more than one treatment surface. In such embodiments, the probe can include an adjustment mechanism for drawing the treatment surfaces closer together, or for moving them farther apart. According to some embodiments, the adjustment mechanism can allow the treatment surfaces to be moved such that they are adjacent to one another and form a continuous treatment surface, like the treatment surface 18 in FIG. 1A. The two treatment surfaces may be positioned parallel to one another. Alternatively, the treatment surfaces may be positioned at an angle with respect to one another and to the probe, such that they are better configured to make contact with the surface of the target tissue.

The treatment surfaces may include one or more cooling elements and heating elements. The cooling elements and heating elements may enable cooling and/or heating, respectively, of an entire treatment surface at once. Alternatively, each cooling element or heating element may enable cooling or heating of multiple portions of the treatment surface, individually or simultaneously. Each of the treatment surfaces may also have a plurality of cooling elements and/or heating elements that can cool or heat, respectively, sections of the treatment surface separately and/or in succession. For example, the treatment surface 20 may be divided into a number of sections along its length. Cooling may be applied for a first period of time in the first section, and once the first period of time ends, cooling of the first section may end, while cooling of the second section may begin. This may continue along the length of the treatment tip, until all sections of the treatment surface 20 have undergone cooling. The treatment surface 22 may undergo a similar heating process at the same time, or the processes may be conducted at different times. Multiple treatments can occur at one location. In such instances, heating may precede, follow or occur concurrently with the cooling such that the target tissue is maintained at a desired therapeutic temperature. By heating the tissue, ablation of the tissue due to unintentional freezing of the tissue is prevented. In some embodiments, the target tissue is cooled and no heating is applied. In some embodiments, the heating element is a radiofrequency energy element.

Further, the treatment surfaces may be configured such that individual sections can undergo cooling. For example, the first section may undergo cooling prior to heating of the same first section. The cooling may cease while the heating of the first section takes place. During this period, the second section may undergo a cooling process. When the heating of the first section ends, cooling of the first section may resume for a period of time, while heating of the next section begins. This process may continue along the length of the treatment surfaces. This process is purely exemplary, and other combinations and patterns of heating and cooling may also be used. The controller 13 may control the cooling elements and RF energy heating elements to achieve the desired treatment pattern and to ensure that the therapeutic temperature is maintained.

In embodiments having more than one treatment surface, the total surface area of the multiple treatment surfaces can be between about 0.5 cm$^2$ and about 6 cm$^2$. One of skill in the art may contemplate other surface areas that are appropriate for treating specific target tissues, and would understand the embodiments of the invention to include devices having these configurations.

An example system suitable for use in practicing the methods of the invention include a non-invasive system for promoting correction of an aesthetic or functional defect in a target tissue, the system having: a controller coupled to a probe for promoting wound healing in the target tissue, the probe having a distal end configured for non-invasive contact with a surface of the target tissue and having a proximal end coupled to the controller; and at least one aesthetic or functional defect treatment parameter the at least one aesthetic or functional defect treatment parameter selected to achieve a predetermined temperature for a predetermined time period in a target tissue to induce remodeling of the target tissue and promote wound healing. The controller coupled to the probe is configured to cool the target tissue based on the at least one aesthetic or functional defect treatment parameter to induce a remodeling of the target tissue for improvement of the aesthetic or functional defect.

Another example system includes the non-invasive system above, further including the probe, wherein the probe includes: a treatment tip configured for non-invasive contact with a surface of a target tissue, the treatment tip including: an epithelium-contacting treatment surface; a cooling element in thermal communication with the epithelium-contacting treatment surface; and a heating element in thermal communication with the epithelium-contacting treatment surface. The controller is further configured to be in communication with the cooling element and the heating element, and the controller is further configured to control the cooling element and the heating element to cool or heat a first portion of the epithelium-contacting treatment surface while simultaneously heating or cooling a second portion of the epithelium-contacting treatment surface.

An example apparatus suitable for use in practicing the methods of the invention include an apparatus including three parts: a console that controls the therapeutic application of energy, a handpiece that connects to the console, and a treatment tip that attaches to the handpiece and applies the energy to the desired point of therapy on a patient's skin. In such embodiments, the console and handpiece are durable multi-use pieces of equipment. The treatment tip, according to some embodiments, is a onetime use only disposable device. The complete apparatus applies cold therapy to a treatment area. The surface of the treatment tip can have multiple shapes, i.e., rectangular, circular, cylindrical, etc. In some embodiments, the surface area of the treatment tip is approximately 1 square inch. In some embodiments, cold therapy is applied to the area being treated. In some embodiments, the cold therapy is accomplished by evaporating compressed or liquid $N_2$, $CO_2$ or $NO_2$ or a cryogenic refrigerant directed on or near the surface of the treatment tip and then applying the treatment tip to the surface of the tissue by direct contact. The surface of the treatment area is cooled to a desired therapeutic temperature. The temperature is kept within the therapeutic range by applying RF energy via electrodes located at the distal end of the treatment tip. The bipolar electrodes allow the RF energy to heat the treatment area only to a shallow depth—equivalent to the same depth the cold therapy is being applied. Monopolar electrodes allow the RF energy to heat the tissue to a deeper depth, equivalent to and beyond the depth the cold therapy is being applied. The RF energy is throttled in such a way that the treatment area stays within a therapeutic temperature. The therapeutic temperature is established through validation. The therapeutic temperature is low enough to provide positive therapeutic effect but not so low that it ablates the area treated. The system prevents the tissue from falling below the therapeutic temperature creating a cryoablation by applying RF energy to warm the skin. The cold therapy triggers the tissue's wound/healing mechanism. That wound/heal mechanism can reduce or eliminate the effect of skin injuries or flaws.

In the example apparatus above, the controller, including the integrated controller described above, may include a display that is configured to display information about the procedure, the energy and/or heat, the coolant, the treatment tip, the handle and other components of the system. This information may be displayed on the front of the integrated controller, and the controller may present the information with audio signals as well. The display may also be set by the controller to display error information (including error codes) based on the status of the various system components (e.g., coolant level, contact with skin, RF generator status, etc.).

In some examples of the system described above, the controller is configured to execute a programed or customizable treatment protocol designed to achieve a predetermined temperature for a predetermined time period in a target tissue to induce remodeling of the target tissue and promote wound healing. The controller instructs the cooling and heating elements to initiate a programed treatment protocol including sequenced pulse duration, pulse timing, and pulse coordinates on a target tissue to induce remodeling of the target tissue and promote wound healing.

One of skill in the art can envision that customizable treatment protocols can be programmed to achieve efficient remodeling and wound healing in specific target tissues. In some embodiments, the treatment protocol includes a plurality of "pulses" or "treatment passes" (used interchangeably throughout) to deliver a cooling agent to the target tissue. These pulses can be spatially overlapping to substantially cover the target treatment area. The extent to which the pulses overlap, as well as the number of pulses used to cover the target tissue area, may depend on the size, location, and number of the cooling and heating element(s), as well as the size, location, and shape of the targeted tissue area.

The method and apparatus, as provided by embodiments of the invention, are non-invasive or minimally invasive and substantially non-ablative of targeted tissues. The nature of the engagement between the apparatus and targeted tissues is that of contacting a treatment tip to a surface region of a target tissue. Through such contact, the apparatus delivers a cooling agent to the surface region, and subsequently cools the target tissue to a therapeutic temperature while preventing ablation. In some embodiments, heat is also applied to assist with the maintenance of the desired therapeutic temperature. In some embodiments, a second cooling step follows or partially overlaps with the heating step.

In some embodiments, the cooling mechanism of the apparatus includes a lumen adapted to accommodate a cooling fluid conveyed to nozzles, which cool the cooling element of treatment tip of the probe. Embodiments of the method thus provide for contacting a contact site on a surface of a target tissue using a treatment tip, the treatment tip having the capability both to cool one or more tissue layers of the target tissue and to (optionally) heat the same one or more layers of the target tissue. In some embodiments, the cooling fluid cools the treatment tip of the apparatus, as provided by embodiments of the invention; in turn, the surface of the cooled treatment tip draws energy from the one or more tissue layers of the target tissue that the treatment tip contacts. In some embodiments, the cooling element is configured to apply a cooling agent to a surface of the target tissue. In some embodiments, the cooling agent is selected from the group consisting of compressed liquid $CO_2$, compressed liquid $NO_2$, a hydrofluorocarbon, water, a thermoelectric cooler and an ultra-low temperature cryogen.

As provided by embodiments of the invention, one or more tissue layers of a target tissue may be cooled to a temperature range of about 5.0 degrees Celsius to about 25.0 degrees Celsius, or more preferably to between about 10.0 degrees Celsius to about 20.0 degrees Celsius.

During the first cooling step, the tissue is cooled from about a nominal temperature (about 38.0 degrees Celsius) to a temperature that is in a range of about 3.0 degrees Celsius to about 25.0 degrees Celsius below nominal tissue temp (e.g., a range of about 35.0 degrees Celsius to about 13.0 degrees Celsius). In examples with an energy application step after the first cooling step, e.g., a non-cooling step, the temperature of the tissue is raised during the energy application step to a temperature that is in a range of about 5.0 degrees Celsius to about 30.0 degrees Celsius above the temperature at the end of the first cooling step (e.g., a range of about 18.0 degrees Celsius to about 43.0 degrees Celsius). In the second cooling step, the tissue is again cooled to a temperature that is in a range of about 3.0 degrees Celsius to about 25.0 degrees Celsius below the nominal tissue temperature (e.g., a range of about 35.0 degrees Celsius to about 13.0 degrees Celsius). The term "about" includes a temperature that is up to 1.5 degrees Celsius higher and 1.5 degrees Celsius lower than the provided values. The ranges encompass all discrete values within the endpoints and also encompass the endpoints.

The temperatures provide in the aforementioned method, and in other exemplary methods herein, may be measured as a surface temperature of the target tissue. In some cases, the temperatures measured may be subsurface tissue temperatures. In examples where the temperatures are measured for subsurface tissues, the temperatures may be about 2 degrees Celsius lower on the lower end of the range.

In an embodiment of the invention, RF energy is delivered to cooled target tissue. In such an embodiment, RF pulse sequence(s) preceding, following or occurring concurrently with a cooling step serves to protect the cooled one or more tissue layers of the target tissue from ablation as a result of inadvertently cooling the tissue(s) to a temperature below the therapeutic temperature. Importantly, the RF energy heats the same one or more layers of tissue cooled.

In some embodiments of the invention, cooling and maintaining the one or more tissue layers at a therapeutic temperature provokes a cytokine cascade including various heat shock proteins and/or cold shock proteins. This results in remodeling of the target tissue and improvement of the aesthetic or functional defect of the target tissue. In some embodiments, the RF energy is delivered by a monopolar RF energy source.

In some embodiments, the probe and system described above includes a monopolar RF energy heating element. Other embodiments may make use of other forms of energy, such as bipolar RF energy, microwave, laser, or ultrasound.

The energy delivery element may be any of monopolar RF electrodes, bipolar RF electrodes, a microwave emitter, a laser, or an ultrasound emitter. The RF electrodes (whether monopolar or bipolar), in some embodiments, are capacitive electrodes, which capacitively couple to the mucosal epithelium. The RF electrodes (whether monopolar or bipolar), without limiting the scope of the invention, may have a thickness in the range of about 0.01 to about 1.0 mm. In some embodiments the electrodes can be separated by a predetermined distance. Such a distance can be a function of the depth of tissue penetration desired. In some such embodiments, the electrodes can be separated by a distance between 1 mm to 30 mm, and more preferably between 5 mm and 15 mm.

Additionally, the electrodes may be equipped with an integrated EEROM (Electrically Erasable Read Only Memory, also known as EEPROM) programmable memory chip at any suitable location within the treatment tip (not shown). Such a chip may provide identifying information or other information about the operational status or configuration parameters of the RF electrodes to the system. Such parameters may include, by way of example, but not limited to, the type and size of the electrodes, the number of times the energy delivery element has been fired, times or durations (e.g., of energy delivery, of the times between energy delivery, the total treatment time, etc.), temperatures, temperature limits, transition temperatures, energy application, energy limits, current applied, current limits, voltage applied, voltage limits, arming parameters, and the like. Additionally, thermistors (thermal sensors) may be provided at each corner of the RF electrodes, or otherwise in close proximity to the electrodes, to provide feedback to the system on the temperature at their location.

In some embodiments, the cooling element and heating element are positioned on an end of the treatment tip. The cooling element and heating element can have dimensions adapted to making approximately flat contact with the surface of the target tissue. Various lengths, widths, shapes and formations can readily be envisioned and designed to best conform the cooling element and heating element to a specific target tissue.

According to some embodiments of the invention, the treatment surface has a flat configuration. In other embodiments the treatment surface has a radial configuration.

In some embodiments, the apparatus is included in a larger electronic system with features known in the art. Embodiments may include a power source, a cooling source or energy source that feeds the cooling element in the treatment tip, and/or a RF power source that feeds energy to an RF energy generator and energy flows therefrom to RF electrodes in the treatment tip. The power source may provide energy to a heating source, cooling source, the RF source, etc. In some examples, RF waves may be produced in a range from 3 kHz to 300 GHz. A multiplexer measures current, voltage and temperature, at the thermal sensors associated with each RF electrode. The multiplexer is driven by a controller, which can be a digital or analog controller, or a computer with software. The controller may turn the cooling source, the RF power source, and/or power sources to other features of the system on and off. The controller may determine the length of each cooling, non-cooling, and/or heating period in a given "pulse" or "treatment pass" (used interchangeably throughout). The controller may provide multiple different types of pulses that may vary in the duration of cooling or heating. The controller may provide an indication that a pulse has ended, for example, by providing a visual or audio cue. When the controller is a computer it can include a CPU coupled through a system bus. On the system there may also be a keyboard, disk drive, or other non-volatile memory systems, a display, and other peripherals, as are well known in the art. Also coupled to the bus may be a program memory and a data memory.

In some embodiments, the system includes an operator interface including operator controls and a display. The controller can be coupled to different types of imaging systems including, for example, but not limited to, ultrasonic transceivers, thermal sensors, and impedance monitors. Current and voltage are used to calculate impedance. A diagnostic phase can be initially run to determine the level of treatment activity. This can be done through ultrasound as well as other means. Diagnostics can be performed both before and after treatment.

Other variations of treatment tip design and associated methods can be employed to achieve the objectives of the invention without departing from the scope of the invention, as will be appreciated by those skilled in the art. The shape and dimensions of the tip can also be adjusted, as desired, to enhance the effectiveness of the treatment taking into consideration physiological and anatomical information. While various embodiments of the present invention have been shown and described herein, it will be obvious to those skilled in the art that such embodiments are provided by way of example only. Although the description has offered the theory that heat shock and/or cold shock protein-mediated responses play a role in tissue remodeling, such discussion has been offered simply as a possible theory of how the invention works and as an aid in describing the invention. It should be understood that any such theories and interpretation do not bind or limit the claims with regard to tissue remodeling brought about by the practice of the invention. Numerous variations, changes, and substitutions will now occur to those skilled in the art without departing from the invention. It should be understood that various alternatives to the embodiments of the invention described herein may be employed in practicing the invention. It is intended that the scope of the invention, methods and structures within the scope of the invention includes equivalents.

Methods

Some embodiments of the invention relate a method for aesthetic treatment, including the steps: non-invasively cooling a surface of a target tissue; and cooling one or more tissue layers of the target tissue to a predetermined therapeutic temperature and/or for a period of time. The step of non-invasively cooling is performed such that cryoablation of the one or more tissue layers of the target tissue does not occur.

Some embodiments of the invention relate the method above, further including a step of non-cooling following the cooling step. In some embodiments the step of non-cooling includes a step of non-invasively applying energy to the surface of the target tissue. In some embodiments, the step of non-invasively applying energy to the surface of the target tissue results in heating the target tissue one or more tissue layers of the target tissue to maintain a temperature of the one or more tissue layers above a temperature at which cryoablation occurs.

Some embodiments of the invention relate to the method above, where the target tissue is non-invasively cooled to a second predetermined therapeutic temperature and/or for a second period of time. for a second period of time. This second cooling step follows the step of non-cooling above.

In some examples, a method for treating urinary stress incontinence with therapeutic cooling a plurality of target tissues in a subject includes non-invasively cooling the plurality of target tissues and remodeling one or more submucosal regions of the plurality of target tissues to treat the subject for urinary stress incontinence. The plurality of target tissues are located within 4 predetermined quadrants around a vaginal canal. The plurality of target tissues include 40 target tissue locations, such that each of the 4 predetermined quadrants includes 10 target tissue locations. Non-invasively cooling includes applying at least 10 treatment passes in each of the 4 predetermined quadrants. Each of the at least 10 treatment passes includes applying, in a predetermined order, 1 to 5 cooling periods to each of the 10 target tissue locations in each of the 4 predetermined quadrants. The non-invasively cooling a plurality of target tissues further includes applying up to 20 treatment passes to two or more target tissue locations located alongside a urethra of the subject, each of said 20 treatment passes including applying a cooling period.

As mentioned, the method includes applying at least 10 treatment passes in each of the 4 predetermined quadrants. This step includes executing a first series of 5 treatment passes in each of the 4 predetermined quadrants and executing a second series of 5 treatment passes in each of the 4 predetermined quadrants. The first series of 5 treatment passes in each quadrant is completed before the second series of 5 treatment passes in each of the 4 predetermined quadrants is initiated. Each of the first series of 5 treatment passes and each the second series of 5 treatment passes includes applying in a predetermined order one cooling period to each of the 10 target tissue locations in each of the 4 predetermined quadrants.

As mentioned, the method includes applying up to 20 treatment passes to two or more target tissues located alongside the urethra of the subject. This step includes delivering a first series of 10 treatment passes to the two or more target tissues located alongside the urethra and delivering a second series of 10 treatment passes to the two or more target tissues located alongside the urethra. The first series of 10 or more treatment passes is delivered after executing the first series of 5 treatment passes in each of the 4 predetermined quadrants. The second series of 10 or more treatment passes is delivered after executing the second series of 5 treatment passes in each of the 4 predetermined quadrants.

As mentioned, the method includes executing each treatment pass of the first series of 5 treatment passes in each of the 4 predetermined quadrants. This step includes applying, in a predetermined order, a cooling step to each of a first set of 5 target tissue locations in each of the 4 predetermined quadrants such that each target tissue location of the first set of 5 target tissue locations at least partially overlaps with an adjacent target tissue location. Executing each treatment pass of the second series of 5 treatment passes in each of the 4 predetermined quadrants includes applying in a predetermined order a cooling step to each of a second set of 5 target tissue locations in each of the 4 predetermined quadrants, such that each target tissue location of the second set of 5 target tissue locations at least partially overlaps with an adjacent target tissue location.

According to the method, each target tissue location of the second set of 5 target tissue locations in each of the 4 predetermined quadrants is proximal to each target tissue location of the first set of 5 target tissue locations in each of the 4 predetermined quadrants.

According to the method, the first series of 10 treatment passes and the second series of 10 treatment passes are delivered to two target tissue regions. A first target tissue region of the two target tissue regions is located on a first side of the urethra. A second target tissue region of the two target tissue regions is located on a second side of the urethra. Each treatment pass of the first series of 10 treatment passes and the second series of 10 treatment passes are applied in an alternating manner to the first target tissue region and to the second target tissue region.

As mentioned, the method includes executing the first series of 5 treatment passes in each of the 4 predetermined quadrants. This step includes executing 5 treatment passes in a first quadrant, executing 5 treatment passes in a second quadrant after executing 5 treatment passes in the first quadrant, executing 5 treatment passes in a third quadrant after executing 5 treatment passes in the second quadrant, and executing 5 treatment passes in a fourth quadrant after executing 5 treatment passes in the third quadrant.

According to the method, the 4 predetermined quadrants include a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position. The urethra of the subject is located at the 12 o'clock position.

In the method, each of the cooling periods is applied for up to 2.0 seconds. Each of the cooling periods is applied for up to 1.5 seconds. Each of the cooling periods cools the each of the plurality of target tissues to a surface temperature of between 13 degrees Celsius and 35 degree Celsius. Each of the 10 treatment passes and each of the 20 treatment passes includes a non-cooling step following each of the cooling periods.

The non-cooling step can include non-invasively heating each of the plurality of target tissues for a period of time. The non-invasively heating each of the plurality of target tissues for a period of time includes delivering radiofrequency energy to each of the plurality of target tissues. The non-invasively heating each of the plurality of target tissues for a period of time includes heating each of the plurality of target tissues to a surface temperature between 18.0 degrees Celsius to 43.0 degrees Celsius for between 0.0-8.0 seconds.

In the method, the non-cooling step is followed by a second cooling step. The second cooling step is applied for between 2.0 seconds and 8.0 seconds. The second cooling step cools each of the plurality of target tissues to a surface temperature of between 13 degrees Celsius and 35 degrees Celsius.

In the method, the plurality of target tissues are located at a first position, a second position, a third position, and a fourth position, and wherein the first position is located 0 to 2 cm beyond the hymenal ring, the second position is located 1 to 3 cm beyond the hymenal ring, the third position is located 1 to 3 cm beyond the hymenal ring, and the fourth position is located 2 to 4 cm beyond the hymenal ring.

The at least 10 treatment passes includes one hundred passes at the first position, ten passes at the second position, one hundred passes at the third position, and ten passes at the fourth position.

In the method, the remodeling of the one or more sub-mucosal regions of the plurality of target tissues to treat the subject for urinary stress incontinence may be caused only by the non-invasive cooling. Alternatively, or additionally, the non-invasively cooling is the only energy application to the plurality of target tissues. Alternatively, or additionally, the non-invasively cooling is the dominate energy application to the plurality of target tissues, such that, the non-invasive cooling provides the treatment of the urinary stress incontinence and any other energy application applied that is not non-invasive cooling does not provide the treatment of the urinary stress incontinence.

Some embodiments of the invention relate to the method described above, where the one or more tissue layers cooled is a surface tissue layer. It is understood by one of ordinary skill in the art that various types of tissues can be present as surface tissues. The type of tissue is not limited to particular type of tissue or to only one type of tissue. For instance, in some embodiments the surface tissue is a mucosal layer, or an epidermis layer, or a dermis layer.

Some embodiments of the invention relate to the method described above, where a combination of surface tissues are targeted. For instance, in some embodiments multiple surface tissues of the vagina are targeted including the epithelium of the mucosal tissue of the vaginal opening and labium minora (for example) and the epidermis layer or dermis layer of the labia majora. In some embodiments, the various tissues of the anal canal are targeted, including the mucosal tissues of the upper anal canal and the epithelium of the lower anal canal. In some embodiments, tissues of the rectum are targeted. In some embodiments, tissues of the anus are targeted. In some embodiments, the oral mucosa of the mouth is targeted as is the epithelium of the lips outside of the mouth.

Some embodiments of the invention relate to the method described above, where tissue layers exposed due to injury are targeted. For instance, in some embodiments, dermis tissue exposed as a result of injury to an overlying epidermis layer is targeted. Similarly, loose connective tissue in mucosal tissue is targeted in the event of injury to an overlying epithelial layer.

Some embodiments of the invention relate to the method described above, where mucosal tissues are also treated. In such embodiments, the methods include the step of treating one or more of a vaginal mucosa, an oral mucosa, a naso-pharyngeal mucosa, an esophageal mucosa, a rectal mucosa or an anal mucosa.

Some embodiments of the invention relate to the method described above, where the step of cooling one or more tissues includes a first cooling step that includes cooling the one or more tissue layers to a temperature between about 35.0 degrees Celsius to about 13.0 degrees Celsius. In examples with an energy application step after the first cooling step, the temperature of the tissue is raised during the energy application step to a temperature that is in a range of about 18.0 degrees Celsius to about 43.0 degrees Celsius.

In the second cooling step, the tissue is again cooled to a temperature that is in a range of about 35.0 degrees Celsius to about 13.0 degrees Celsius. The term "about" includes a temperature that is up to 1.5 degrees Celsius higher and 1.5 degrees Celsius lower than the provided values. The ranges encompass all discrete values within the endpoints and also encompass the endpoints.

Some embodiments of the invention relate to the method described above, where the step of non-invasively applying a cooling agent includes contacting the one or more tissue layers of the target tissue with a treatment tip during a procedure. In such embodiments, the treatment tip includes a cooling mechanism.

Some embodiments of the invention relate to the method described above, where the step of non-invasively applying a cooling agent includes contacting one or more tissue layers of the target tissue with a treatment tip at two or more contact sites during a procedure. In some embodiments, the step(s) of contacting the one or more tissue layers is repeated at least twice during a procedure such that each of the two or more contact sites is contacted at least twice.

Some embodiments of the invention relate to the method described above, where the step of non-invasively applying a cooling agent includes evaporating compressed liquid $CO_2$, or $NO_2$ on a surface of a treatment tip and contacting the surface tip to one or more tissue layers of a target tissue.

Some embodiments of the invention relate to the method described above, where the cooling agent is liquid $N_2$, liquid $CO_2$, liquid $NO_2$, a hydrofluorocarbon, water, a thermoelectric cooler or an ultra-low temperature cryogen.

Some embodiments of the invention relate to the method described above, where the step of cooling the one or more tissue layers triggers a wound-healing reaction in the one or more tissue layers of the target tissue. In some embodiments, the wound-healing includes the generation of collagen.

Some embodiments of the invention relate to the method described above, where the step of cooling the one or more tissue layers induces a remodeling of the one or more tissue layers. In some embodiments, remodeling includes a release of heat shock and/or cold shock proteins. In some embodiments, at least some of the remodeling occurs during the cooling of the one or more tissue layers of the target tissue.

Some embodiments of the invention relate to the method described above, where the step of non-invasively applying a cooling agent is done for between 2 seconds to 8 seconds in the first cooling step and about 0 seconds to about 8 seconds in the second cooling step. The non-cooling step is about 0 seconds to about 8 seconds. The term "about" includes a time that is up to 0.5 seconds higher and 0.5 seconds lower than the provided values. The ranges encompass all discrete values within the endpoints and also encompass the endpoints. In examples where the duration is 0 seconds, this may be understood to indicate the step is not performed.

In some embodiments, the cooling agent is applied continuously for a desired amount of time. In some embodiments, the cooling agent is applied during a sequence of two or more treatment passes, wherein each treatment pass is the same duration of time or a different duration of time. In such embodiments, the treatment pass are separated by a predetermined duration of time.

Some embodiments of the invention relate to the method described above, where the method for aesthetic treatment further includes the step of treating an aesthetic injury or functional defect in a subject.

Some embodiments of the invention relate to the method described above, also including a step of non-invasively applying a heating agent to the surface of the target tissue; and heating the one or more tissue layers of the target tissue to maintain a temperature of the one or more tissue layers above a temperature at which cryoablation occurs.

Some embodiments of the invention relate to the method described above, where the step of non-invasively applying a heating agent is carried out with a probe having a bipolar electrode for applying radiofrequency energy as the heating agent. The applied RF energy creates a band of heat. The heat band depth in the targeted tissue is ½ the distance between the 2 electrodes on the bipolar electrode (conventional)—and that band of heat warms tissue at the given depth and prevents the cold treatment from passing deeper into the tissue. In such embodiments, the cooler surface tissue is located above the band of heat on the surface layer of the tissue. The band of heat serves as a barrier to the cold to prevent the cold from going deeper into the tissue. In such embodiments, different layers of tissue are cooled and heated, with the cooling being done to the surface layer of the tissue and the heating occurring deeper in the tissue below the cold tissue surface layer.

Some embodiments of the invention relate to the method described above, where the step of non-invasively applying a cooling agent is performed over a first period of time, the step of non-invasively applying a heating agent is performed over a second period of time, and the first period of time overlaps at least partially with the second period of time.

Some embodiments of the invention relate to the method described above, where the step of non-invasively applying a cooling agent commences before the step of non-invasively applying a heating agent commences. Also, the step of non-invasively applying the heating agent continues until the step of non-invasively applying a cooling agent is terminated.

Some embodiments of the invention relate to the method described above, where the step of non-invasively applying the heating agent occurs concurrently with the step of non-invasively applying the cooling agent.

Some embodiments of the invention relate to the method described above, where a second step of non-invasively applying a cooling agent is performed over a third period of time. The third period of time at least partially overlaps with the second period of time and then continues after the second period of time ends. In some embodiments, the third period of time does not commence until after the second period of tie ends.

Some embodiments of the invention relate to the method described above, where the step of non-invasively applying a heating agent also includes delivering of at least one of radiofrequency energy, microwave energy, laser energy, or ultrasound energy.

Some embodiments of the invention relate to the method described above, where a combination of surface tissues are targeted. For instance, in some embodiments multiple surface tissues of the vagina are targeted including the epithelium of the mucosal tissue of the vaginal opening and labium minora (for example) and the epidermis layer or dermis layer of the labia majora. In some embodiments, the various tissues of the anal canal are targeted, including the mucosal tissues of the upper anal canal and the epithelium of the lower anal canal. In some embodiments, tissues of the rectum are targeted. In some embodiments, tissues of the anus are targeted. In some embodiments, the oral mucosa of the mouth is targeted as is the epithelium of the lips outside of the mouth.

Some embodiments of the invention relate to the method described above, where the target tissue specifically includes female genital tissue. In some embodiments, individual structures including the female genital are targeted. In some embodiments, multiple structures are targeted. Structures including the female genital are understood by one of ordinary skill in the art and include, by way of non-limiting example: the clitoral hood, the clitoris, the labium minorum, the vaginal opening, the perineum, and the labia majora.

Some embodiments of the invention specifically relate to methods for aesthetic treatment, including non-invasively applying a cooling agent to a surface of a target tissue, where the target tissue is vaginal tissue. In such embodiments, multiple surface tissues of the vagina can be targeted including the epithelium of the mucosal tissue of the vaginal opening and labium minora (for example) and the epidermis layer or dermis layer of the labia majora. Various other tissues and structures within and outside of the vagina can be targeted for therapy.

Some embodiments of the invention include non-invasive treatment of lower portions of the vagina. The lower portions of the vagina are the portions immediately inward from the introitus. An embodiment of the invention provides a non-surgical and non-invasive method for aesthetic treatment. Such a treatment includes non-invasively applying a cooling agent to a surface of a target tissue in at least one lower portion of the vagina and cooling one or more tissue layers of the target tissue to a predetermined therapeutic temperature. In such embodiments, applying the cooling agent is performed such that cryoablation of the one or more layers of the target tissue does not occur. In some embodiments, the target tissue area is inside the vagina directly proximal to the hymenal ring and the cooling of the target tissue induces remodeling of the target tissue. Thus, according to an embodiment of the invention, the portion of the vagina to be treated is a region between the hymen and a position located no further than about 4 to 6 cm inward from the hymen.

Figure 2:
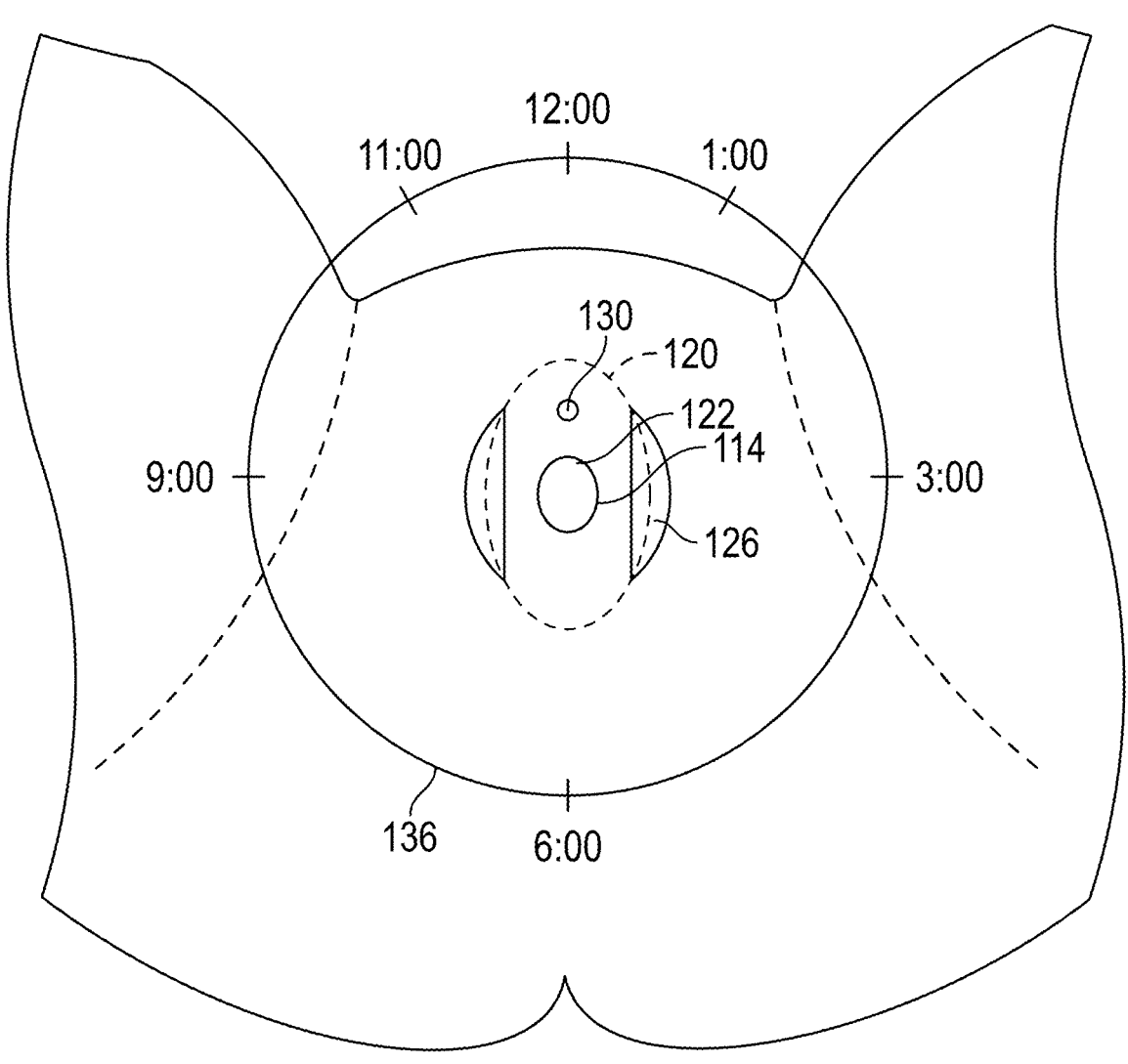
FIG. 2 illustrates a schematic view of female genitalia, as well as an orienting clock to provide a circumferential reference scheme for the vaginal wall, according to an embodiment of the present disclosure.

According to an embodiment of the invention, the anatomical areas of the female genitalia treated include the vagina and the introitus, the opening of the vagina. With more specific regard to the vagina, embodiments of the method include treating the lower portion of the vagina, a portion extending from the introitus to a location from about 4 cm to about 6 cm inward from the introitus. With regard to the circumference of the inner wall of the vagina, a clock-position reference scheme is helpful. FIG. 2 shows such a schematic, 136. The urethra lies next to the anterior wall of the vagina. Thus, the location of the vaginal wall nearest the urethra and urethral opening may be considered 12 o'clock in FIG. 2.

The vagina is a fibromuscular tube, lined with stratified squamous epithelium that connects the external and internal organs of the female reproductive system. The vagina runs obliquely upwards and backwards at an angle of about 45 degrees between the bladder in front and the rectum and anus behind. In an adult female the anterior wall is about 7.5 cm long and the posterior wall is about 9 cm long. The difference in length is due to the angle of insertion of the cervix through the anterior wall. FIG. 2 is a schematic view of female genitalia depicting the mucosal epithelial surfaces as well as an orienting clock 136 to provide a circumferential reference scheme for the vagina wall. FIG. 2 shows the urethra 130, Hart's line 120, the vaginal opening 122, the introitus 114, and the labium minora 126.

The mucosal epithelium of vulvar tissue outside the vagina and the introitus includes the labia minora, or that portion of the vulva extending outward from the introitus to Hart's line, the boundary where mucosal epithelium and labial skin meet. The mucosal epithelium and the skin, while contiguous, are embryologically and histologically distinct. The portion of the female genitalia that is covered by epithelium is also substantially defined by the bounds of the vestibule, which extends outward or down from the hymenal ring at the top of the vagina, radially beyond the introitus, including the portion of labia minora located within Hart's line 120. The target tissue of some embodiments of this invention include the connective tissue underlying these mucosal epithelial surfaces of the genitalia which, progressing down from the epithelial surface, are known as the lamina propria and the muscularis, respectively. The lamina propria includes a mixture of cell types that populate connective tissue, such as fibroblasts, and the muscularis is a layer of smooth muscle. Collagen is secreted or deposited into the extracellular space in these tissues by cells such as fibroblasts. These described target tissue layers below the epithelium overlay deeper tissues, including endopelvic fascia, which are not a target tissue for embodiments of the present invention.

The method and apparatus, as provided by embodiments of the invention are non-invasive and substantially non-ablative of genital tissue. The nature of the engagement between the apparatus and genital tissue is that of contacting a treatment tip to an epithelial surface of the genital tissue. Through such contact, the apparatus cools one or more layers of a target tissue. In some embodiments, heat is also applied before, during or after the cooling to prevent the tissues from being damaged due to falling below a therapeutic temperature, or below a temperature associated with ablation of the tissue.

According to an embodiment of the invention, the anatomical areas of the human oral and nasal cavities are treated.

According to an embodiment of the invention, the anatomical areas of the human anus, anal canal and/or rectum are treated.

According to some embodiments of the invention, a "pulse" or "treatment pass" (used interchangeably throughout) refers to application of a cooling agent for a first period of time, a non-cooling period of a second period of time, and a second application of a cooling agent for a third period of time. In some embodiments, the non-cooling period includes delivering energy to a target tissue to heat the target tissue and/or related layers. Some embodiments can include treatment protocols having a variety of pulses or treatment passes applied to a target tissue (e.g., a first pulse for applying a cooling agent followed by a second pulse applying a cooling and a heating agent simultaneously).

In some embodiments where a cooling agent and a heating agent are applied, the cooling agent and the heating agent can be applied simultaneously in one pulse or treatment pass, or applied individually in separate pulses or treatment passes. In embodiments where the cooling agent and the heating agent are applied in separate treatment passes, the individual treatment passes can partially overlap in timing of execution such that a first treatment pass does not terminate before a second treatment pass commences.

The duration of each treatment pass will vary depending on the nature of the cooling agent or heating agent applied, the type of tissue targeted (as different tissues will require varying amount of time to reach a desired therapeutic temperature), and the duration of time the target tissue is intended to maintain a therapeutic temperature. In general, the duration of a treatment pass will vary from 0.1 second to 300 seconds. In addition, in some embodiments, a plurality of treatment passes or varying durations are applied. For example, a procedure may include a first cooling period of 1 second, followed by a heating period of 1 second, followed by a second cooling period of 5 seconds.

According to some embodiments, a procedure may include a period of cooling of the target tissue, followed by a period of rest, and then a second period of cooling. In such embodiments, each "pulse" or "treatment pass" may include a period of cooling of the target tissue, followed by a period of rest, and then a second period of cooling. The duration of each of the cooling and rest periods may be the same, or may vary.

According to some embodiments, a procedure may include a period of cooling of the target tissue, followed by a period of non-cooling, which may be heating, and then a second period of cooling. In such embodiments, each "pulse" or "treatment pass" may include a period of cooling of the target tissue, followed by a period of non-cooling, which may be heating, and then a second period of cooling. In some embodiments, the period of heating may at least partially overlap with at least one of the cooling periods, or may entirely overlap with the first or second cooling period. Also, the duration of each of the cooling and heating periods may be the same, or may vary. In some examples, the method may include cooling only and no heating. In some examples, the method may be cooling dominant such that the cooling temperatures provide the therapeutic treatment to the target tissues.

The cooling of target tissue, per some embodiments of the invention, includes lowering the temperature of the target tissue to as low as about 35.0 degrees Celsius to about 13.0 degrees Celsius. That is, the temperature of the target tissue may be lowered to a temperature that is about 3 degrees Celsius to about 25 degrees Celsius lower than a nominal tissue temperature, where nominal tissue temperature is about 38.0 degrees Celsius. The term "about" includes a temperature that is up to 1.5 degrees Celsius higher and 1.5 degrees Celsius lower than the provided values. The ranges encompass all discrete values within the endpoints and also encompass the endpoints.

In some examples, the target tissue may be lowered by about 11 degrees Celsius, by about 12 degrees Celsius, by about 13 degrees Celsius, by about 14 degrees Celsius, or by about 15 degrees Celsius. In some examples, the target tissue may be lowered by a range of about 36 degrees Celsius to about 11 degrees Celsius, by a range of about 35 degrees Celsius to about 12 degrees Celsius, by a range of about 34 degrees Celsius to about 13 degrees Celsius, by a range of about 33 degrees Celsius to about 14 degrees Celsius, by a range of about 30 degrees Celsius to about 13 degrees Celsius, by a range of about 25 degrees Celsius to about 13 degrees Celsius, by a range of about 25 degrees Celsius to about 13 degrees Celsius, or by a range of about 20 degrees Celsius to about 13 degrees Celsius. The term "about" includes a temperature that is up to 1.5 degrees Celsius higher and 1.5 degrees Celsius lower than the provided values. The ranges encompass all discrete values within the endpoints and also encompass the endpoints.

In some embodiments, each treatment pass can include a first cooling step which includes applying a cooling agent for a first period of time. The first period of time can range from about 2 seconds to about 8 seconds. In some embodiments, each treatment pass also includes a period of non-cooling following the first cooling step. The period of non-cooling can range from about 0 seconds to about 8 seconds. In some embodiments, this period of non-cooling includes heating the tissue to a predetermined temperate and/or for a predetermined period of time. In some embodiments, each treatment pass also includes a second period of cooling following the period of non-cooling. This second period of cooling can range from about 0 seconds to about 8 seconds. The term "about" includes a time that is up to 0.5 seconds higher and 0.5 seconds lower than the provided values. The ranges encompass all discrete values within the endpoints and also encompass the endpoints. In examples where the duration is 0 seconds, this may be understood to indicate the step is not performed.

In some embodiments, a treatment protocol includes 1, 2, 3, 4, 5 or more treatment passes. In some embodiments, each treatment pass is completed consecutively with little or no lag time, while in other embodiments there is a predetermined lag time between each treatment pass. In some embodiments, a total of about 220 treatment passes are applied to a plurality of target locations around the vaginal canal over the course of 1, 2, 3, 4, 5 or more treatment pass during a single treatment session. According to some embodiments, one or more of the plurality of treatment passes delivers energy to a target tissue. Non-limiting examples of energy include radiofrequency (RF) energy, microwave energy, and ultrasound energy.

In some embodiments, a plurality of target locations are divided among predetermined quadrants around the vaginal canal. In such embodiments, a first quadrant is from 12 o'clock to 3 o'clock, a second quadrant is from 3 o'clock to 6 o'clock, a third quadrant is from 6 o'clock to 9 o'clock, and a fourth quadrant is from 9 o'clock to 12 o'clock, where the urethra is located at 12 o'clock. In such embodiments, each quadrant can have 1, 2, 3, 4, 5, 6 or more target locations.

According to some embodiments of the invention, the treatment passes can be applied to a plurality of target tissue locations as illustrated in FIGS. 3A-3D. FIGS. 3A-3D show four non-limiting example schematics, with each of FIGS. 3A-3D representing a schematic showing a cross-section of the vaginal canal 302 and urethral opening 304 and targeted tissue locations on the vaginal canal. Also shown for orientation is the hymen 306, and the cervix 308. In such embodiments, the circumference of the vaginal canal is divided into four quadrants with a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and where the urethra of the subject is located at the 12 o'clock position.

Figure 3A:
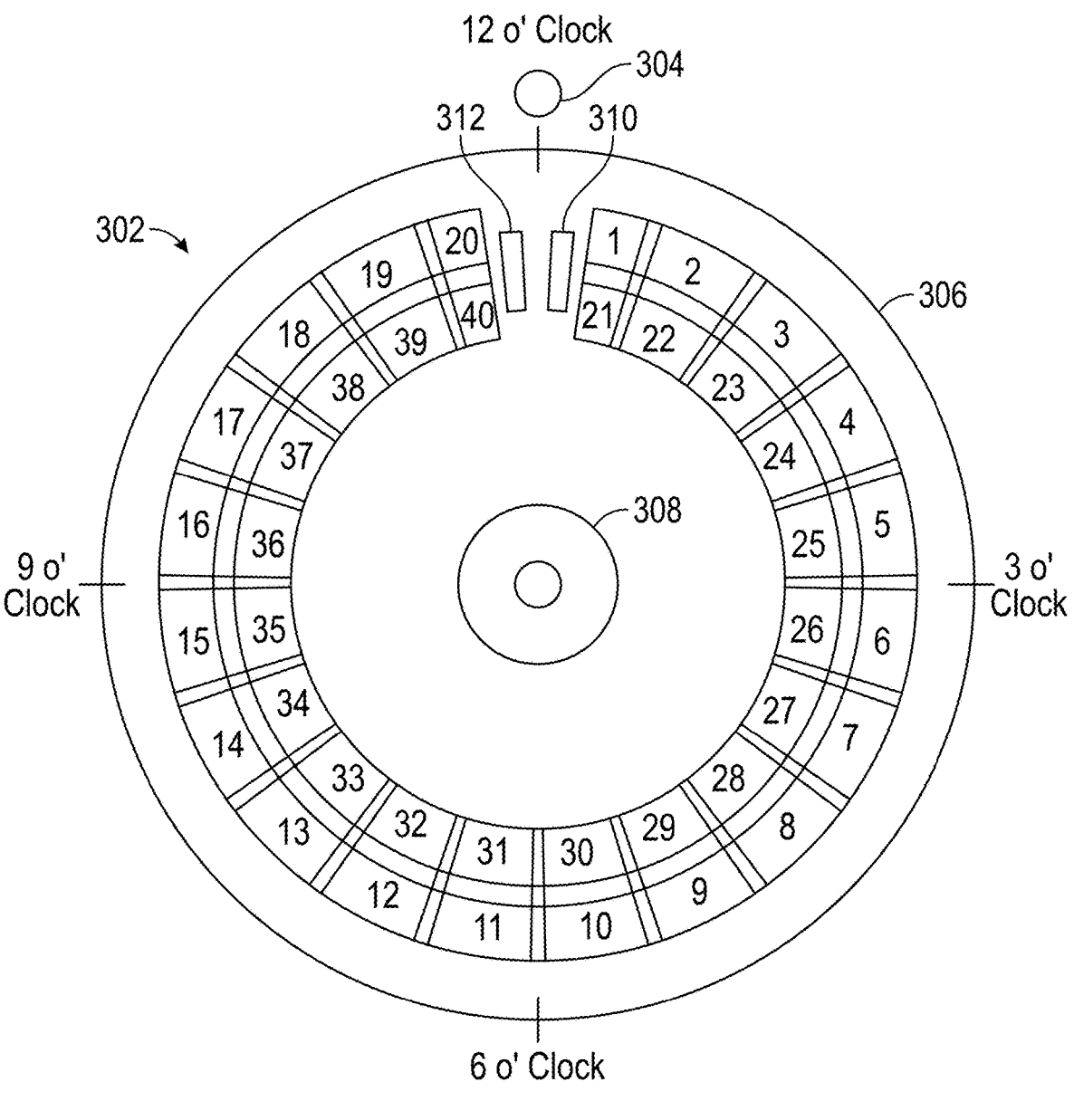
FIG. 3A illustrates an example mapping grid depicting a plurality of target tissue locations, according to an embodiment of the present disclosure.
Figure 3B:
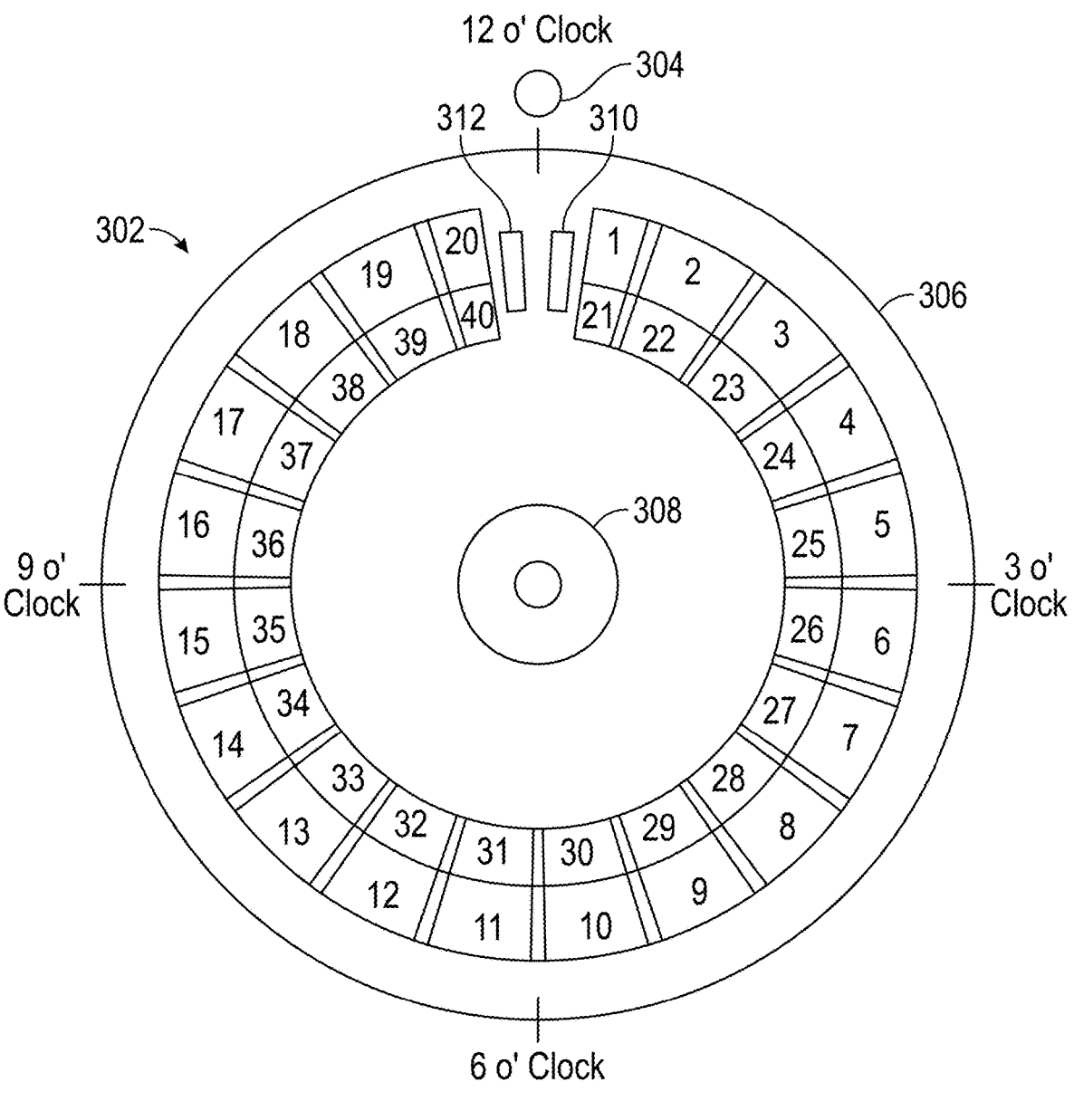
FIG. 3B illustrates an example mapping grid depicting a plurality of target tissue locations, according to an embodiment of the present disclosure.
Figure 3C:
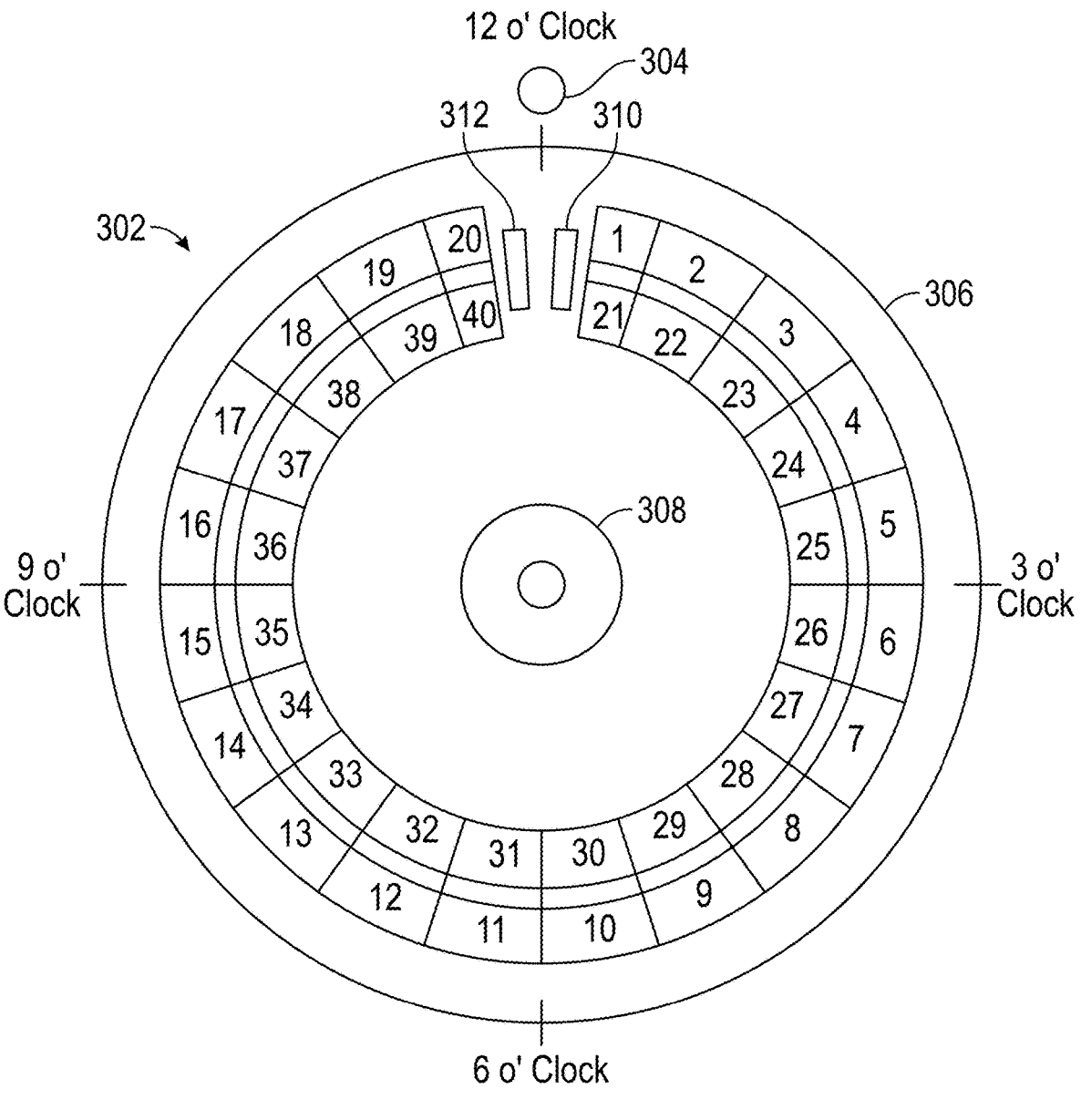
FIG. 3C illustrates an example mapping grid depicting a plurality of target tissue locations, according to an embodiment of the present disclosure.
Figure 3D:
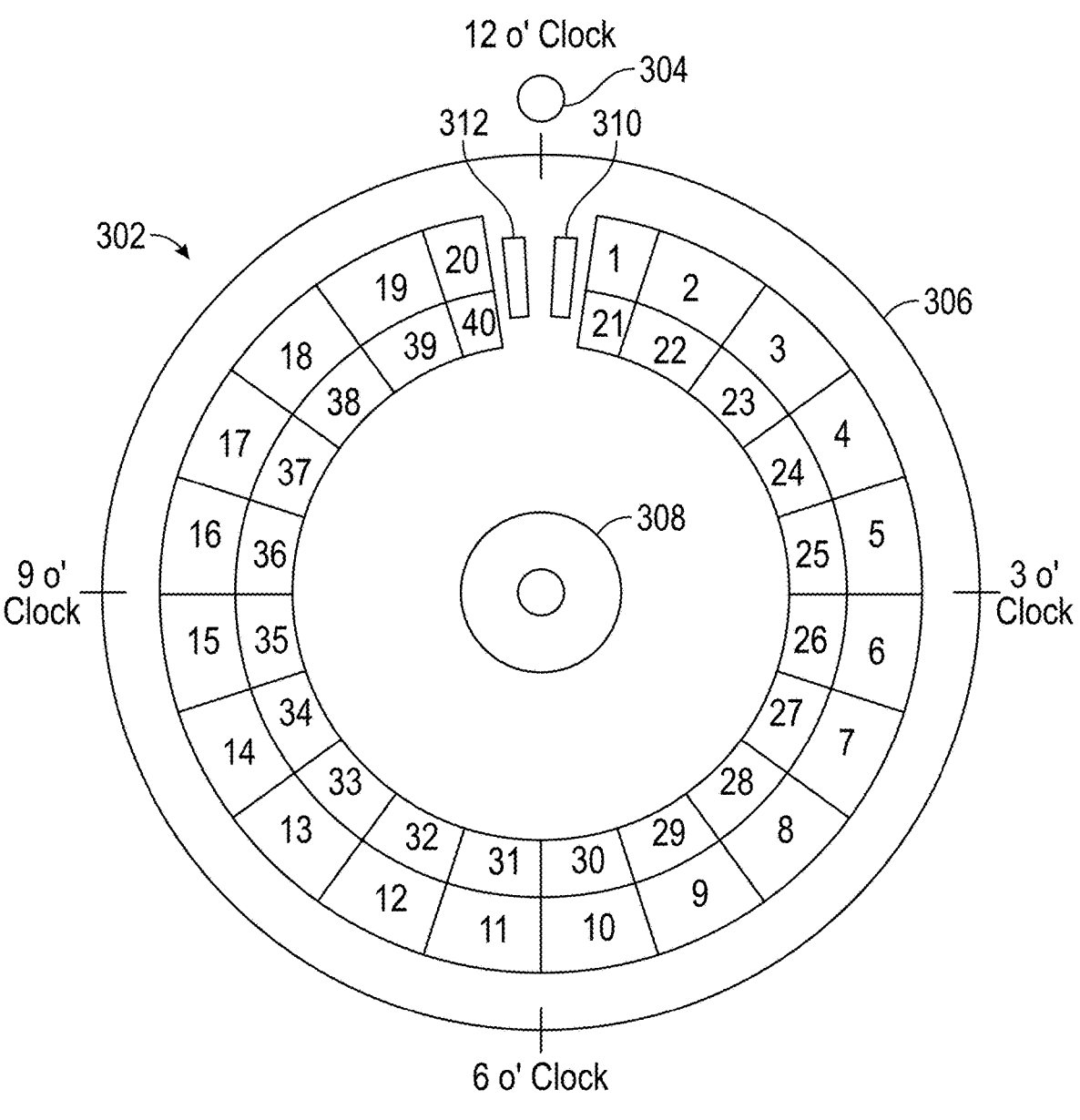
FIG. 3D illustrates an example mapping grid depicting a plurality of target tissue locations, according to an embodiment of the present disclosure.

In FIGS. 3A-3D, each tissue target location is depicted by numbers 1-40. In FIGS. 3A-3D, tissue target locations 1-20 are proximal to the introitus, while tissue target locations 21-40 are located deeper into the vaginal canal and are proximal to tissue target locations 1-20. In some embodiments the tissue target locations overlap at least partially with circumferentially adjacent tissue target locations and with tissue target locations located above or below as seen in FIG. 3A. In some embodiments the tissue target locations overlap at least partially with circumferentially adjacent tissue target locations without overlap between target locations located above or below as seen in FIG. 3B. In some embodiments the tissue target locations overlap at least partially with tissue target locations located above or below without overlap between circumferentially adjacent tissue target locations as seen in FIG. 3C. In some embodiments the tissue target locations do not overlap with either adjacent tissue target locations or with tissue target locations located above or below as seen in FIG. 3D. In some embodiments, tissue target locations 310 located alongside the right side of the urethra and tissue target locations 312 located alongside the left side of the urethra are also treated. Embodiments of the invention are not limited to the schematics and tissue target locations depicted in FIGS. 3A-3D.

As summarized above, in some embodiments, a given treatment area is treated during a single procedure during an office visit. Aspects of the methods further include repetitions of such procedures, typically on another day, when the effects of the previous procedure may be evaluated. From such evaluation, judgment may be made with regard to re-treating a particular previously treated area, or proceeding to treat other areas. Thus, as provided by embodiments of the method, one or more procedures during follow-up visits may variously include treating the same treatment area, treating an entirely different treatment area, or treating an overlapping treatment area, partially the same as the previous area, and partially different.

Other variations of treatment tip design and associated methods can be employed to achieve the objectives of the invention without departing from the scope of the invention, as will be appreciated by those skilled in the art. For example, the shape and dimensions of the treatment tip can also be adjusted, as desired, to enhance the effectiveness of the treatment, taking into consideration physiological and anatomical information.

While various embodiments of the present invention have been shown and described herein, those skilled in the art will understand that such embodiments are provided by way of example only. Although the description has offered various theories, such theories have been offered simply as possible theories of how the invention works and as an aid in describing the invention; however, it should be understood that such theories and interpretation do not bind or limit the claims with regard to tissue remodeling brought about by the practice of the invention. Numerous variations, changes, and substitutions will occur to those skilled in the art without departing from the invention. It should be understood that various alternatives to the embodiments of the invention described herein may be employed in practicing the invention. It is intended that the scope of the invention, methods and structures within the scope of the invention includes equivalents.

In some embodiments, a procedure, such as would take place in a visit to a medical office, would typically include contacting the surface of the target tissue with a treatment tip on a probe and applying a sequence of pulses. During the same procedure, the treatment tip may be returned to the same contact point multiple times. The total treatment time may be about 30 minutes.

In some embodiments, subsequent treatment(s) can be performed within one month, or at a time later than one month from a first treatment session.

Some embodiments of the method include heating the target tissue using a radiant energy source, typically an RF energy source, but other embodiments may use microwave, ultrasound energy, laser, or magnetic potential energy sources. Some embodiments include contacting the mucosal epithelium with a treatment tip that has an energy delivering element as well as a cooling mechanism.

The method according to some embodiments includes remodeling of the target tissue. The cooling of one or more tissue layers within the target tissue to a predetermined temperature for a predetermined period of time results an immediate or nearly immediate effect of the activation of heat shock proteins and/or cold shock proteins, resulting in initiation of remodeling of the one or more tissue layers of the target tissue. In other embodiments of the invention, the cooling of the one or more tissue layers during a treatment procedure is understood to result in a subsequent remodeling of the target tissue as part of a biological process that may take place over the course of weeks or months following the procedure.

In another aspect, the apparatus can include three parts: a console that controls the therapeutic application of energy, a handpiece that connects to the console, a treatment tip that attaches to the handpiece and applies the energy to the desired point of therapy on the patient's skin. The console and handpiece can be durable multi-use pieces of equipment. The treatment tip can be a onetime use disposable device. The complete system can apply cold therapy to the treatment area. The surface of the treatment tip can have multiple shapes, i.e., rectangular, circular, cylindrical, etc. The surface area of the treatment tip (for therapy application) can be approximately 1 square inch, for example. Cold therapy can be applied to the area being treated. The cold can be generated by evaporating compressed or liquid $N_2$, $CO_2$ or $NO_2$, directed to the surface of the treatment tip and then applied to the surface of the tissue by direct contact. For example, cryogen can be used to cool the tip or the back of an energy element inside the tip, such as an electrode, and the cool surface of the treatment tip is applied to the surface of the tissue. The treatment area of the tissue can be cooled to the desired therapeutic temperature. The temperature of the treatment area can be kept within the therapeutic range by applying energy, such as RF energy via an electrode, at the distal end of the treatment tip. A monopolar electrode allows the RF energy to heat the treatment area tissue deeply while a bipolar electrode allow the RF energy to heat the treatment area only to a shallow depth, in one aspect, equivalent to the same depth the cold therapy is being applied. The RF energy is throttled in such a way that the treatment area stays within a therapeutic level. The therapeutic temperature level is described herein in accordance with the principles of the invention. The therapeutic level is low enough to provide positive therapeutic effect but not so low that it ablates the area treated. The therapeutic effect is described herein in accordance with the principles of the invention. The system prevents the cold from falling below the therapeutic level creating a cryo-ablation by using the application of the RF energy to heat and/or warm the tissue. The cold therapy triggers a wound/healing mechanism as described herein. That wound/heal mechanism can reduce or eliminate the effect of skin injuries or flaws. In some examples, only the cooling provides the therapeutic treatment of the target tissue.

The following examples are non-limiting examples of therapeutic methods for treating tissue.

Example 1—Therapeutic Cooling Method for Treating Urinary Stress Incontinence

Figure 4A:
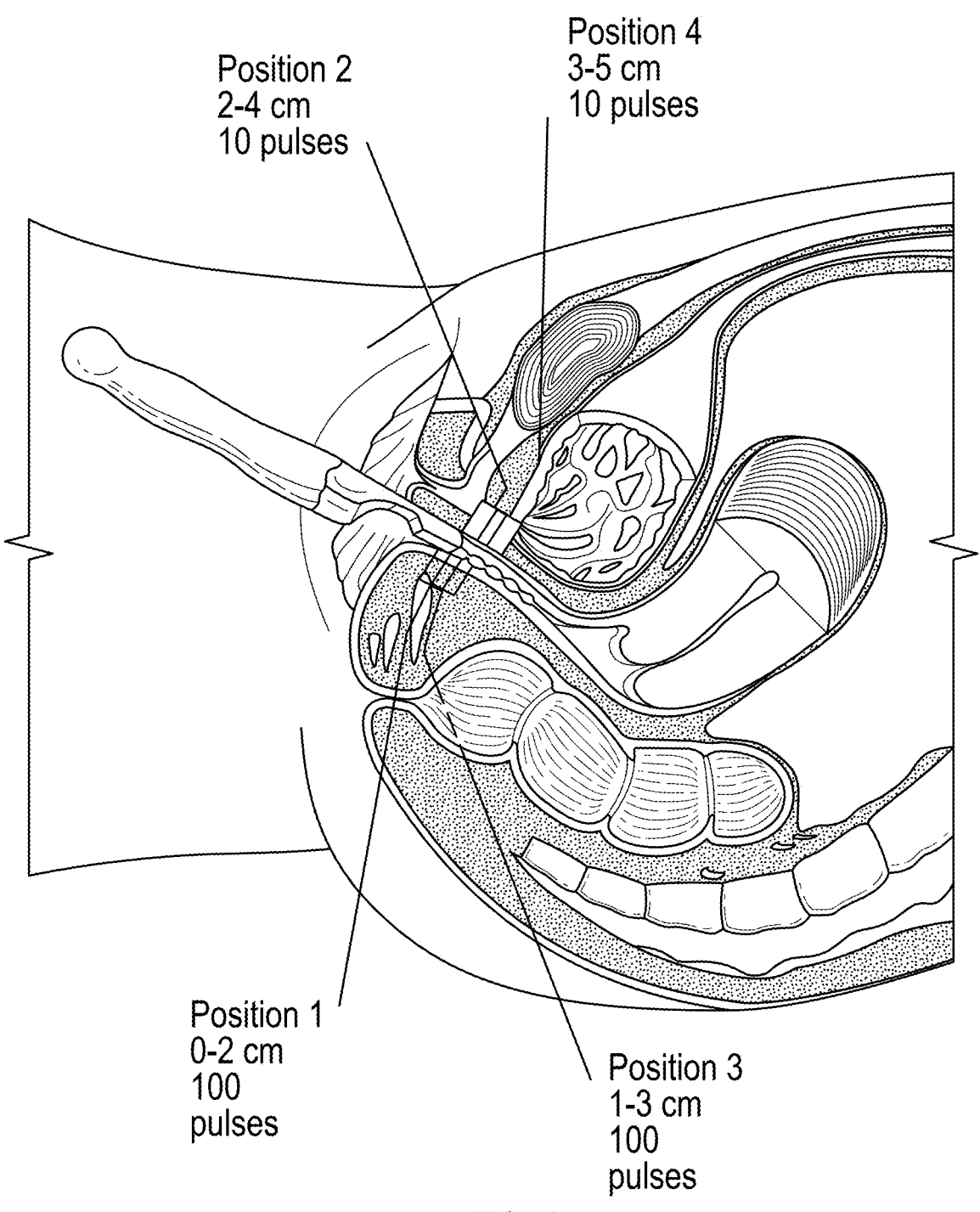
FIG. 4A illustrates a treatment diagram, according to an embodiment of the present disclosure.
Figure 4B:
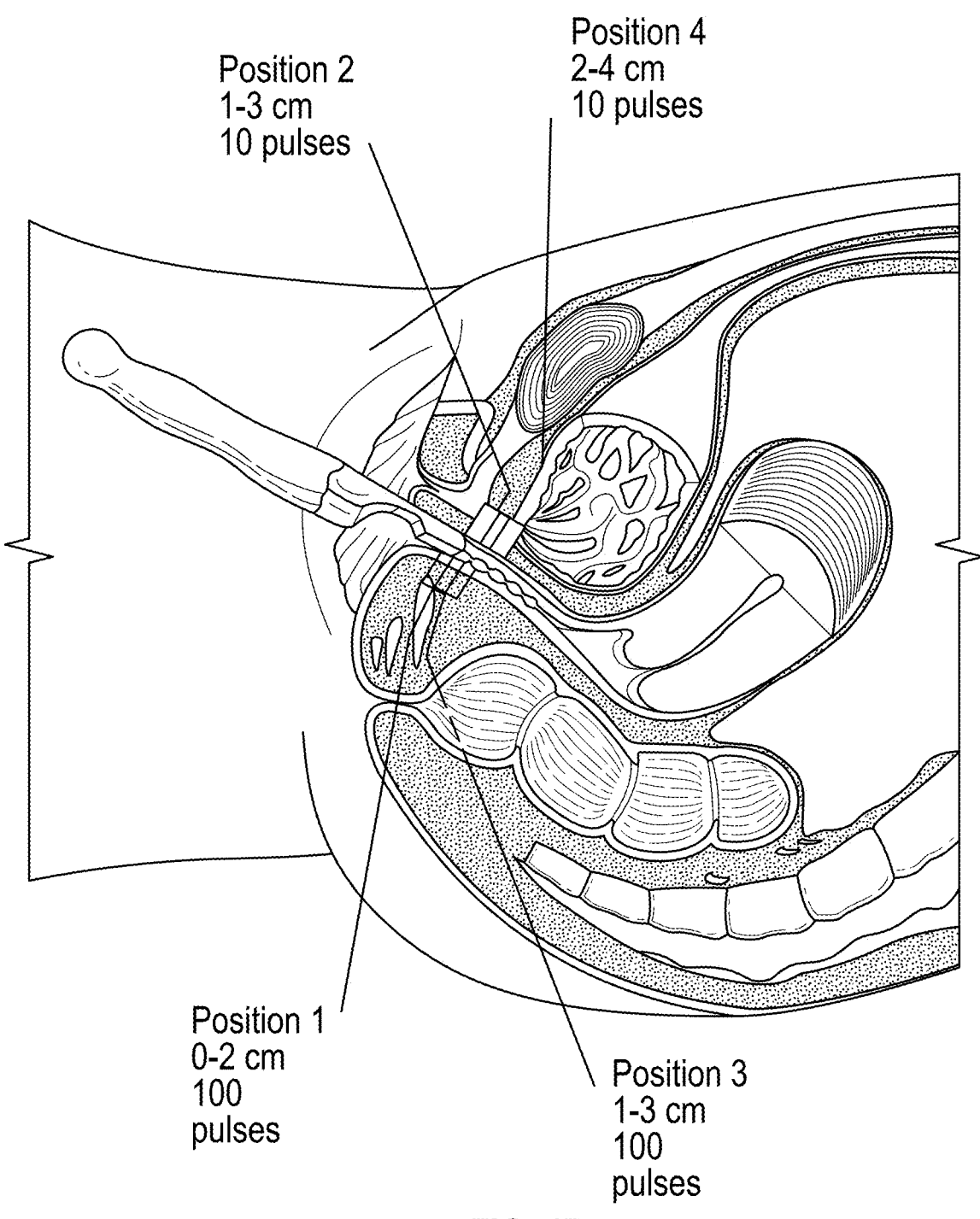
FIG. 4B illustrates a treatment diagram, according to an embodiment of the present disclosure

A method for treating urinary stress incontinence in a subject includes the following treatment protocol, and is also outlined as described with respect to FIGS. 4A and 4B.

In the method of example 1, a subject, such as, for example, a patient, is placed on an examination table in a dorsal lithotomy position. According to the protocol of example 1, each treatment pass or pulse includes a first period of cooling, a non-cooling period, and a second period of cooling. The applied energy (e.g., cooling) during the first period of cooling is applied for a range of 1 to 2 seconds and cools or lowers the temperature of the tissue to a range of 25 degrees Celsius to 29 degrees Celsius. The non-cooling period is performed for 0.5 to 1.5 seconds. During the non-cooling period, 1 Joule of energy may be applied to maintain the tissue at a temperature of 31 degrees Celsius to 33 degrees Celsius. The non-cooling period may include heating the tissue or may not include heating the tissue. The applied energy (e.g., cooling) during the second period of cooling is applied for 4 seconds and cools or lowers the temperature of the tissue to 25 degrees Celsius to 29 degrees Celsius. The temperatures of the method of example 1 are surface temperatures of the tissue.

The treatment area is divided into quadrants of the vaginal introitus with the area directly beneath the urethra excluded, in a manner similar to or the same as described with respect to FIGS. 3A to 3D.

Position 1: 0-2 cm beyond hymenal ring (100 treatment passes). The treatment tip placement is beyond hymenal ring: proximal edge 0 cm, distal edge 2 cm. The first set of 100 treatment passes is applied to the area just behind the hymenal ring using the quadrant approach. Each quadrant is treated with 5 consecutive passes of 5 locations of treatment passes for a total of 25 treatment passes/quadrant. Treatment passes are applied in a clockwise fashion with an overlap of ~0.5 cm, starting from the 1:00 position. Once a quadrant is fully treated with 25 treatment passes, the next quadrant is treated, until all 4 quadrants are treated, ending at the 11:00 position. The treatment area should avoid the area overlying the urethra, by using the urethral sparing window and avoiding treatment between 11 o'clock and 1 o'clock. For example, referring to any of FIGS. 3A to 3D, location 1 is pulsed, location 2 is pulsed, location 3 is pulsed, location 4 is pulsed, and the location 5 is pulsed. The process is then repeated starting at location 1, until 25 total pulses or passes are provided to locations 1 to 5 in the first quadrant. Then treatment is moved to the second quadrant and locations 6 to 10 are treated in the same manner for 25 total pulses, and so on in the third and fourth quadrants for a total of 100 total pulses, 25 in each quadrant. Accordingly, locations 1 to 20 of FIGS. 3A to 3D are understood to be located within "position 1."

Position 2: 2-4 cm beyond hymenal ring (10 treatment passes total). The treatment tip placement is beyond hymenal ring: proximal edge 2 cm, distal edge 4 cm. The second depth of treatment involves positioning the proximal edge of the treatment tip window ~2 cm behind the hymenal ring. Five treatment passes are applied directly to the right of the urethra (e.g., in the area of location 310 in FIGS. 3A to 3D) and five treatment passes are applied directly to the left of the urethra (e.g., in the area of location 312 in FIGS. 3A to 3D) observing the urethral sparing window between 11 o'clock and 1 o'clock. That is, no treatment occurs in the space between 11 o'clock and 1 o'clock.

The treatment may be paused for two minutes between the position 2 and position 3.

Position 3: 1-3 cm beyond hymenal ring (100 treatment passes), Position 3 is ~1 cm overlapped with Position 1. The treatment tip placement beyond hymenal ring: proximal edge 1 cm, distal edge 3 cm (there should be ~1 cm overlap between Position 1 and Position 3). The third set (Position 3) of treatment passes (which includes 100 treatment passes) are applied in a similar fashion to Position 1, but at ~1 cm deeper than Position 1. This provides an ~1 cm overlap of treatment passes. The treatment area should avoid the area overlying the urethra, by using the urethral sparing window and avoiding treatment between 11 o'clock and 1 o'clock. For example, referring to any of FIGS. 3A to 3D, location 21 is pulsed, location 22 is pulsed, location 23 is pulsed, location 24 is pulsed, and the location 25 is pulsed. The process is then repeated starting at location 21, until 25 total pulses or passes are provided to locations 21 to 25 in the first quadrant. Then treatment is moved to the second quadrant and locations 26 to 30 are treated in the same manner for 25 total pulses, and so on in the third and fourth quadrants for 100 total pulses, 25 in each quadrant. Accordingly, locations 21 to 40 of FIGS. 3A to 3D are understood to be located within "position 3."

Position 4: 3-5 cm beyond hymenal ring (10 treatment passes), Position 4 is ~1 cm overlapped with Position 2. The treatment tip placement is beyond hymenal ring: proximal edge 3 cm, distal edge 5 cm (there should be ~1 cm overlap between Position 2 and Position 4). The fourth depth of treatment (Position 4) is applied in a similar fashion to the Position 2, but with the proximal edge of the treatment tip window positioned ~3 cm behind the hymenal ring. Five treatment passes are applied directly to the right of the urethra (e.g., in the area of location 310 in FIGS. 3A to 3D) and five treatment passes are applied directly to the left of the urethra (e.g., in the area of location 312 in FIGS. 3A to 3D) observing the urethral sparing window between 11 o'clock and 1 o'clock. That is, no treatment occurs in the space between 11 o'clock and 1 o'clock.

The treatment is completed when a total of 220 treatment passes have been applied.

Referring to FIG. 4B, the same or similar procedure as FIG. 4A may occur, with the positions differing. In the case of FIG. 4B, Position 1 occurs at 0-2 cm beyond the hymenal ring, Position 2 occurs at 1-3 cm beyond the hymenal ring, Position 3 occurs at 1-3 cm beyond the hymenal ring, and position 4 occurs at 2-4 cm beyond the hymenal ring.

In other examples, the 100 pulses or passes at position 1 may occur in a full sequential circumference from position 1 to position 20, and then repeated from position 1 to position 20 until 100 pulses are performed. The process may be similar for position 3, moving from location 21 to location 40 in a full sequential circumference.

Example 2—Study Using a Therapeutic Cooling
Method for Treating Urinary Stress Incontinence Stress Urinary Incontinence (SUI) Clinical Study History The trial was a randomized, double-blinded, and cool-treatment protocol ("sham" protocol) trial with a planned enrollment of approximately 100 subjects at up to ten study sites in Canada. Subjects were randomized in a 2:1 ratio for active and sham treatments and the trial featured a primary endpoint of baseline to six-month improvement on the one-hour pad weight test. Also, a smaller study was performed in which 36 patients were enrolled in a single-arm feasibility study in patients with mild-to-moderate SUI (1 g-50 g of leakage on the one-hour pad weight test) at baseline and this yielded positive six-month follow-up data. The six-month data showed 69% of patients achieved a 50%+ reduction from baseline, and can be seen in FIG. 5, which also contains the twelve-month data from the study above.

The results looked strong from an absolute treatment effect standpoint, and there was no separation between the heat-treatment protocol ("active") and cold-treatment protocol ("sham") arms. The data showed a median change from baseline on the one-hour pad weight test at six months post-treatment was ~8.0 g in the active group of 66 subjects (baseline median 12.8 g) and ~8.0 g in the sham-control group of 33 subjects (baseline median 12.9 g).

After the initial studies disclosed in FIG. 5, additional data was obtained from the study including the following exploratory endpoints shown in Table 1 below. The treatment effect is very similar on all the reported outcomes. In addition, no serious device-related events were reported, the groups were well-balanced, and early termination from the study was, as expected, at ~14%.

TABLE 1

| Results from follow-up study comparing heat-treatment protocol ("active") to cold-treatment protocol ("sham") | | |
|---|---|---|
| Group/Measure | Baseline (median) | Improvement |
| Active (n = 66) | | |
| 1-Hour Pad Weight Test | 12.8 g | −77.2% |
| 24-Hour Pad Weight Test | 19.8 g | −71.0% |
| 3 Day Diary Incontinence Episodes | 8.0 | −83.3% |
| UDI-6 | 55.6 | −44.4% |
| I-QOL | 52.8 | 35.6% |
| ICIQ-UI-SF | 14.0 | −46.2% |
| Sham (n = 33) | | |
| 1-Hour Pad Weight Test | 12.9 g | −81.0% |
| 24-Hour Pad Weight Test | 21.8 g | −61.3% |
| 3 Day Diary Incontinence Episodes | 8.0 | −72.7% |
| UDI-6 | 55.6 | −37.5% |
| I-QOL | 56.8 | 27.1% |
| ICIQ-UI-SF | 13.0 | −33.3% |

In the studies above and below, the "sham" treatment tip delivered cryogen cooling.

FIG. 6 is a graphical representation of the data from FIG. 5 and Table 1 above. Based on the data, it is estimated that one could expect a 70% improvement from baseline on three of the endpoints—the one-hour and 24-hour pad weight tests and the three-day diary of incontinence episodes, but both the CMRF tip and cryo-only tip generated significantly greater improvements on these measures.

The consistency of improvement in both the active treatment and the sham-control (or cold-treatment) groups and the magnitude and duration of these improvements may indicate that the effect is unlikely due to placebo. Anecdotally, clinicians shared their own experiences which were in line with these results.

Example 3

Next, an in-vivo preclinical temperature and tissue study was conducted in three parous ewes (sheep that had given birth at least once). Results of the study, which assessed in-vivo tissue temperature changes and 30-day post-treatment histopathology are shown in FIG. 7 below. The significant temperature changes generated at the introitus sub-mucosa-lamina propria interface (blue line) by both the CMRF tip as well as the cryo-only tip and the consequent increased fibroblast activation seen in the α-smooth muscle actin (α-SMA) staining histopathology in the lower panel for both tips (bottom panel). The new sham tip demonstrated virtually no change in temperature in this tissue and saw no increased fibroblast activation.

Example 4

The results from the parous ewe study discussed above gave confidence to move into a small, three-arm human feasibility study. A three-month feasibility study of 36 patients randomized 1:1:1 between the CMRF tip, the cryo-only tip, and the new inert tip was commenced. However, the COVID-19 pandemic and consequent provider and patient health and safety concerns caused the company to extend the follow-up period to five months rather than the original three.

The three-arm feasibility study achieved its primary efficacy endpoint (change from baseline on the one-hour pad weight test) with no device-related safety issues reported. Results are shown in FIG. 8. Although the secondary endpoints—the three-day voiding diary, 24-hour pad weight test and Incontinence Quality of Life (I-QOL) questionnaire at five months—did not show any separation, this is likely partially due to the quirks of the randomization, which neatly sorted the highest baseline levels into the CMRF (active) group, the next highest into the cryo-cooled "sham" arm, and the lowest into the inert sham arm on both a mean and median basis. Mathematically, larger percentage changes from baseline are easier to achieve when the baseline is a lower absolute number, and in this study the CMRF group had nearly double the baseline one-hour pad weight of the inert sham group. Given the SUI registration trial, discussed next, will use the proportion of patients who achieved a 50% reduction on the one-hour pad weight test in the active arm versus the same proportion in the sham arm, the fact they met the primary endpoint in this feasibility study despite the quirks of the randomization is a positive read-through for the outcome of the pivotal study.

Example 5

With favorable outcomes of the in-vivo preclinical study and the three-arm feasibility study above, it became apparent that the cryo-only sham tip was delivering a therapeutic effect and that the new inert sham tip, was just that—inert. A new study was designed and addressed several study design considerations, clearing to begin enrolling the trial with the trial design described in the "Initial Design" column in Table 2 below. Below, alterations made in the trial design between the initial design and the current design are bolded and italicized; in addition, new secondary endpoints are shown italicized in the right column, while the one that was removed from the initial design is italicized in the left column.

TABLE 2

| New cold-treatment study design | | |
|---|---|---|
| | Initial Design | Current Design |
| Expected Enrollment | 240 | 390 |
| Study Sites | Up to 25 | Up to 30 |
| Randomization | 2 Active: 1 Sham | 2 Active: 1 Sham |
| Primary Endpoint | Proportion of patients experiencing 50%+ reduction on standardized one-hour pad weight test twelve months post-treatment. | Proportion of patients experiencing 50%+ reduction on standardized one-hour pad weight test twelve months post-treatment. |
| Secondary Endpoints | Three-day bladder voiding diary. Change from baseline on Urogenital Distress Inventory-6 (UDI-6). Change from baseline on Incontinence Quality of Life (I-QOL). Change from baseline on International Consultation on Incontinence Modular Questionnaire-Urinary Incontinence Short Form (ICIQ-UI-SF). | Proportion of patients experiencing 50%+ reduction on standardized one-hour pad weight test at three and six months post-treatment. Three-day bladder voiding diary. Change from baseline on Incontinence Quality of Life (I-QOL). Change from baseline on the MESA Questionaire (Medical, Epidemiologic and Social Aspects of Aging). |

TABLE 2-continued

New cold-treatment study design

| Initial Design | Current Design |
| --- | --- |
| | *Change from baseline on Patient Global Impression of Improvement (PGI-1) Questionaire.* Change from baseline on International Consultation on Incontinence Modular Questionaire-Urinary Incontinence Short Form (ICIQ-UI-SF). |

One other item, not listed in the table above is a change to the enrollment criteria, which requires a baseline of 10 grams (equivalent to 10 mL) in the standardized one-hour pad weight test, up from the 5 g in all of the prior *SUI* studies. Regarding the "goalposts", the primary endpoint is the difference in the proportion of patients experiencing a 50%+ reduction on the one-hour pad weight test at twelve months.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. Moreover, features described in connection with one embodiment of the invention may be used in conjunction with other embodiments, even if not explicitly stated above. It is therefore to be understood that, within the scope of the claims and their equivalents, the invention may be practiced otherwise than as specifically described.

We claim:

1. A method for treating urinary stress incontinence with therapeutic cooling a plurality of target tissues in a subject, the method comprising:

non-invasively cooling the plurality of target tissues; and remodeling one or more submucosal regions of the plurality of target tissues to treat the subject for urinary stress incontinence, wherein the plurality of target tissues are located within 4 predetermined quadrants around a vaginal canal, wherein the plurality of target tissues comprise 40 target tissue locations, such that each of the 4 predetermined quadrants comprises 10 target tissue locations, wherein non-invasively cooling comprises applying at least 10 treatment passes in each of the 4 predetermined quadrants, wherein each of the at least 10 treatment passes comprises applying, in a predetermined order, 1 to 5 cooling periods to each of the 10 target tissue locations in each of the 4 predetermined quadrants, and wherein the non-invasively cooling a plurality of target tissues further comprises applying up to 20 treatment passes to two or more target tissue locations located alongside a urethra of the subject, each of said 20 treatment passes comprising applying a cooling period.

2. The method of claim 1, wherein the applying at least 10 treatment passes in each of the 4 predetermined quadrants comprises:

executing a first series of 5 treatment passes in each of the 4 predetermined quadrants; and executing a second series of 5 treatment passes in each of the 4 predetermined quadrants, wherein the first series of 5 treatment passes in each quadrant is completed before the second series of 5 treatment passes in each of the 4 predetermined quadrants is initiated, and wherein each of the first series of 5 treatment passes and each the second series of 5 treatment passes comprises applying in a predetermined order one cooling period to each of the 10 target tissue locations in each of the 4 predetermined quadrants.

3. The method of claim 2, wherein executing the first series of 5 treatment passes in each of the 4 predetermined quadrants comprises:

executing 5 treatment passes in a first quadrant;

executing 5 treatment passes in a second quadrant after executing 5 treatment passes in the first quadrant;

executing 5 treatment passes in a third quadrant after executing 5 treatment passes in the second quadrant; and executing 5 treatment passes in a fourth quadrant after executing 5 treatment passes in the third quadrant.

4. The method of claim 2, wherein the applying up to 20 treatment passes to two or more target tissues located alongside the urethra of the subject comprises:

delivering a first series of 10 treatment passes to the two or more target tissues located alongside the urethra; and delivering a second series of 10 treatment passes to the two or more target tissues located alongside the urethra, wherein the first series of 10 or more treatment passes is delivered after executing the first series of 5 treatment passes in each of the 4 predetermined quadrants, and wherein the second series of 10 or more treatment passes is delivered after executing the second series of 5 treatment passes in each of the 4 predetermined quadrants.

5. The method of claim 4, wherein the first series of 10 treatment passes and the second series of 10 treatment passes are delivered to two target tissue regions, wherein a first target tissue region of the two target tissue regions is located on a first side of the urethra, wherein a second target tissue region of the two target tissue regions is located on a second side of the urethra, and wherein each treatment pass of the first series of 10 treatment passes and the second series of 10 treatment passes are applied in an alternating manner to the first target tissue region and to the second target tissue region.

6. The method of claim 2, wherein executing each treatment pass of the first series of 5 treatment passes in each of the 4 predetermined quadrants comprises applying, in a predetermined order, a cooling step to each of a first set of 5 target tissue locations in each of the 4 predetermined quadrants such that each target tissue location of the first set of 5 target tissue locations at least partially overlaps with an adjacent target tissue location, and wherein executing each treatment pass of the second series of 5 treatment passes in each of the 4 predetermined quadrants comprises applying in a predetermined order a cooling step to each of a second set of 5 target tissue locations in each of the 4 predetermined quadrants, such that each target tissue location of the second set of 5 target tissue locations at least partially overlaps with an adjacent target tissue location.

7. The method of claim 6, wherein each target tissue location of the second set of 5 target tissue locations in each of the 4 predetermined quadrants is proximal to each target tissue location of the first set of 5 target tissue locations in each of the 4 predetermined quadrants.

8. The method of claim 1, wherein the 4 predetermined quadrants comprise a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and wherein the urethra of the subject is located at the 12 o'clock position.

9. The method of claim 1, wherein each of the cooling periods is applied for up to 2.0 seconds.

10. The method of claim 1, wherein each of the cooling periods is applied for up to 1.5 seconds.

11. The method of claim 1, wherein each of the cooling periods cools the each of the plurality of target tissues to a surface temperature of between 13 degrees Celsius and 35 degree Celsius.

12. The method of claim 1, wherein each of the 10 treatment passes and each of the 20 treatment passes comprises a non-cooling step following each of the cooling periods.

13. The method of claim 12, wherein the non-cooling step comprises non-invasively heating each of the plurality of target tissues for a period of time.

14. The method of claim 13, wherein the non-invasively heating each of the plurality of target tissues for a period of time comprises delivering radiofrequency energy to each of the plurality of target tissues.

15. The method of claim 13, wherein the non-invasively heating each of the plurality of target tissues for a period of time comprises heating each of the plurality of target tissues to a surface temperature between 18.0 degrees Celsius to 43.0 degrees Celsius for between 0.0-8.0 seconds.

16. The method of claim 12, wherein the non-cooling step is followed by a second cooling step.

17. The method of claim 16, wherein the second cooling step is applied for between 2.0 seconds and 8.0 seconds.

18. The method of claim 17, wherein the second cooling step cools each of the plurality of target tissues to a surface temperature of between 13 degrees Celsius and 35 degrees Celsius.

19. The method of claim 1, wherein the plurality of target tissues are located at a first position, a second position, a third position, and a fourth position, and wherein the first position is located 0 to 2 cm beyond the hymenal ring, the second position is located 1 to 3 cm beyond the hymenal ring, the third position is located 1 to 3 cm beyond the hymenal ring, and the fourth position is located 2 to 4 cm beyond the hymenal ring.

20. The method of claim 19, wherein the at least 10 treatment passes comprises one hundred passes at the first position, ten passes at the second position, one hundred passes at the third position, and ten passes at the fourth position.

21. The method of claim 1, wherein the remodeling of the one or more submucosal regions of the plurality of target tissues to treat the subject for urinary stress incontinence is caused only by the non-invasive cooling.

22. The method of claim 1, wherein non-invasively cooling is the only energy application to the plurality of target tissues.

23. The method of claim 1, wherein non-invasively cooling is the dominate energy application to the plurality of target tissues, such that, the non-invasive cooling provides the treatment of the urinary stress incontinence and any other energy application applied that is not non-invasive cooling does not provide the treatment of the urinary stress incontinence.

* * * * *